United States Patent [19]

Bau

[11] Patent Number: 5,443,076
[45] Date of Patent: Aug. 22, 1995

[54] MEANS FOR ENHANCING THE PRODUCTIVITY OF VIDEO TELECOMMUNICATION SYSTEMS

[76] Inventor: Marcel Bau, 89 Van Ness Ct., Maplewood, N.J. 07040

[21] Appl. No.: 887,044

[22] Filed: May 22, 1992

[51] Int. Cl.⁶ .......................................... A61B 5/0484
[52] U.S. Cl. ..................................................... 128/731
[58] Field of Search ................................. 128/731–732

[56] References Cited

U.S. PATENT DOCUMENTS

| | | | |
|---|---|---|---|
| 3,855,998 | 12/1974 | Hidalgo-Briceno | 128/732 |
| 3,877,466 | 4/1975 | Montor | 128/732 |
| 4,334,545 | 6/1982 | Shiga | 128/732 |

Primary Examiner—Angela D. Sykes
Attorney, Agent, or Firm—W. Patrick Quast

[57] ABSTRACT

The method and means for enhancing productivity of video telecommunication systems interrelating conferees at physically separated stations that involves the preconditioning of all conferees utilizing a head band providing left and right temporal leads to a versatile EEG-computer linkage, and speakers linked to a synthetic sound generator, exposing individual conferees to a variable light and sound environment where the colors violet to red are associated with sounds ranging in frequency from low to high by exposing the conferee to the sequential flashing of lights in the order violet, blue, green, yellow, orange, red, with the associated sounds, and then in the reverse order to thereby stimulate alpha rhythm functioning respectively in the right and left brain hemispheres, repeating such sequential flashing of lights until essentially uniform and synchronized alpha rhythm functioning is achieved in both brain hemispheres, thereby establishing in the EEG-computer linkage a record of the light and sound conditions which should sustain for the individual the synchronized alpha rhythm brain functioning, and during a conference having each conferee wear a left temporal probe with lead to the EEG-computer linkage and a speaker with lead to the synthetic sound generator, whereby the EEG-computer linkage will provide for the conferee the predetermined and adjusted colored light illumination and sound frequency exposure, the averaged alpha rhythm pattern for conferees at each station being comparatively projected on television screens at both stations, and general conformance in the patterns thus projected indicating that a conference is progressing favorably.

12 Claims, 8 Drawing Sheets

MEANS FOR ENHANCING THE PRODUCTIVITY OF VIDEO TELECOMMUNICATION SYSTEMS

This invention relates to a Telecommunication System for enhancing effectiveness of communication, and hence the productivity of conferences between individuals and/or groups of individuals situated at geographically separate locations. The system involves similarly equipped conference stations at geographically separate locations, interconnected by telephone, television and computer lines activating side by side television screens at each station, and including at each station a television camera having means for instantly switching between a panoramic view of a group of conferees and enlarged views of individual speakers, and with the computer at each station being integrated with a versatile EEG monitor.

More particularly, the invention relates to a telecommunication system of the type described wherein individual participants at each station are provided with variable light and sound environment monitored and controlled by an EEG-computer linkage to provide an environment most conducive to the production of alpha rhythms in the brain of such participants, and with the EEG computer linkages having means for projecting on the second television screen at both stations, the net or averaged brain function pattern for the participants at each station; such brain function patterns utilizing a small portion of the second television screen, and the remainder of the second television screen being available for the projection of charts, graphs, and other visual aids when used by participants at either station, as well as for the projection, from time to time of EEG-computer generated graphics providing a visual indication of the extent to which the conferees are approaching, or deviating from, a "meeting of the minds".

In the use of this telecommunication system the constant projection on the second television screen, preferably in contrasting colors, of the net or average brain functioning pattern of the conferees at each station is of primary significance because, in a smoothly running conference there should be general conformance between the patterns at the two stations. The occurrence of substantial non-conformance in the patterns signals the breakdown of effective communication. If such non-conformance is corrected the conference can be continued, but if the non-conformance persists the conference should be terminated as failing to approach a "meeting of the minds"; and the parties will be guided in making such a decision by the EEG-computer generated graphics.

BACKGROUND OF THE INVENTION

It has long been recognized that the personal involvement in round-the-table conferences between individuals and groups genuinely seeking to reach a point of agreement can be highly productive. This is considered to be due in large part to the unconscious communication taking place by eye contact, physical gestures or body language, and a considerable amount of instantaneous mind to mind communication that is taking place by reason of the close proximity of the participants, and frequently sensed by feelings of elation or euphoria by individual participants as the conference is progressing.

These phenomena provide what is being referred to as real time or instantaneous communication brought on by the fact that the conscious thinking and the unconscious thinking, or "gut reaction", of the individuals have been brought into synchronism to avoid the regular time delays as one is influencing the other.

In the modern world of big governments, multinational corporations, and the general need for global communication, it is increasingly difficult, as well as tremendously expensive and time consuming to take advantage of the above mentioned benefits of round-the-table conferences; and to an increasing extent, needed conferences are being arranged via Integrated Services Digital Networks (I.S.D.N.). Such networks inherently integrate channels of telephone communication, television and computers to establish visual and audio communication between conferring groups and individuals regardless of their physical or geographical separation.

While present technology permits excellent audio and visual communication in such systems, users of such systems report that something is missing, as compared with the experience of round-the-table discussion. There is not the feeling of togetherness, and frequently at the end of a conference it remains questionable whether a true "meeting of the minds" has been reached.

From considerable experience in the field, and extensive searching of the prior art, any prior progress in dealing with this somewhat nebulous but very real problem currently experienced in I.S.D.N. conferencing is unknown.

THE INVENTION

It has now been discovered in accordance with the present invention that the problems above mentioned can be substantially overcome, permitting I.S.D.N. conferences to become more productive by functioning on an essentially real time basis, by providing for each conference participant an EEG controlled and monitored and computer integrated light and sound environment stimulating each individual to experience significantly enhanced alpha rhythm in his brain functioning, to thereby permit synchronization between the participant's conscious and unconscious thinking.

Regarded in certain of its broader aspects, the present invention involves incorporating in an Integrated Services Digital Network (I.S.D.N.), wherein geographically spaced conference stations are interconnected by telephone, television and computer lines, two television screens arranged side by side at one end of each conference station, with a video camera with recording facilities locatead above the television screens, and having means for instantly switching between panoramic viewing of a group of conferees and enlarged viewing of individual speakers, and at the other end of each conference station, providing aligned work areas for a number of conferees, each work area comprising a desk of fixed location, having a compartment for electronic equipment, a movable chair, and an overhead computer controlled variable light source beamed to encompass the occupant of the chair, the several work areas being connected with central versatile EEG and computer equipment, and each work area being provided with a generator of variable synthetic sound, headband means for pre-conference use during computer controlled variations in the light and sound sources to determine through EEG sensing and computer recording the light and sound settings most conducive to alpha rhythm brain functioning of the occupant, an ear mountable device for use during a conference serving the dual purpose of monitoring the individual's brain functioning and supplying soft sound having the pre-determined characterisics, a control button in the work area adapted to be depressed by the occupant when embarking on extended discussion, at least one work area including television means for viewing visual aids being used by the station conferees, one television screen at each station picturing interchangeable panoramic and enlarged individual views of conferees at the remote station, and the second television screen at each station projecting identical images at both stations including on a small portion of the screen area an ongoing graphic comparison of the average brain functioning characteristics of conferees at both stations, and on the major portion of the screen images of interest to both stations including the visual aids as being utilized by conferees at either station, and, from time to time EEG-computer generated graphics providing a visual indication of the extent to which the conferees are approaching, or deviating from a "meeting of the minds".

In adapting novel features of the present invention to a teleconferencing system, there can be considerable variation in the size and placement of equipment, depending upon the number of conferees intended to be utilizing the particular station. A station, for example, may be intended for use only by an individual in contacting groups of conferees at remote locations. On the other hand, the station may be planned to accommodate five or more conferees. Depending upon the size of the station, the size and placement of the television screens should be such that the projected images of individual speakers at the remote station are the size to approximate or exceed the closeness which would be experienced in a round-the-table conference to thereby provide the viewer with the facial expressions and at least limited eye contact with the speaker.

It is considered that as many as five work areas for conferees arranged in alignment facing the television screen, and appropriately spaced with respect to a large screen television, can be effectively viewed by a single television camera located above the television screen with computer controlled angular and zoom adjustments, being able to quickly shift between panoramic views of the conferees and individual enlarged views of particular speakers. If it is contemplated that more than five conferees may be involved in utilizing a particular station, it is considered desirable to accommodate conferees in excess of five in a second row of conferees behind and slightly above the initial row of work areas.

An important part of the present invention is the overhead light source to individually illuminate each work area. This light source will include a white light of variable intensity to provide illumination appropriate for optimum television pick-up, plus individual variable light sources in the colors red, orange, yellow, green, blue and violet. These colored light sources which are computer controlled as hereinafter described can be provided by individual lights or by appropriately colored filters adjustably movable into and out of the primary white light beam. In either instance the light source will include lenses to blend the various colors and focus the combined light beam on the conferee occupying the work area. The light sources will be sufficiently above the conferees to cause no objectionable glare, and sufficiently forward of the conferees to minimize objectionable shadows.

At each work area there is provided a forward compartment for housing essential electronic equipment and a closable opening at the top to house the headband and ear device to be hereinafter discussed and, a rearward extending desk portion with ample leg room beneath it so that the conferee can adjust a movable chair for comfortable occupation of the work area.

The desk portion will be topped with transparent glass or plastic so that an arcuate array of lights, including a white light and lights in the colors red, orange, yellow, green, blue and violet can impinge on the seated conferee. This light source has separate pre-conference and conference uses, as hereinafter described.

Each work station will also include an easy access button in the forward top portion to be activated when the occupant intends to embark on extended discussion to thereby activate the TV camera through a computer to pick up his enlarged image. This control button can suitably be illuminated when activated, and will be deactivated by a second pressing of the button, or by some other conferee depressing his button to modify instructions to the TV camera.

At least one work area will also include a transparent panel and hidden TV camera on which can be placed graphs, charts and other visual aids being utilized by the conferees. In larger conference set-ups, however, this function can be handled at a separate work area outside the range of the main TV camera, and manned by an assistant who is not a conferee.

In the closable compartment at the top forward portion of each work area, there will be a wired headband for pre-conference use, and a wired ear piece for use during the conference. The headband is provided with left and right temporal contacts wired to a versatile EEG machine for recording changes in the user's brain wave patterns, and at least one ear piece through which the user will be exposed to EEG-computer generated synthetic sound of infinitely varied frequency.

For a brief interval prior to the start of a conference, suitably about five minutes, the conferee with headband in place will be exposed to EEG-computer controlled variations in the colored light sources and the sound frequencies for the purpose of determining for the particular conferee the combination of colored light adjustments and sound frequency which is most conducive to alpha brain wave functioning.

As an alternative for having this facility provided at each work area, it may be appropriate in some instances to provide, away from the conference station, separate compartments or cubicles specifically set up for the pre-conference determination of optimum colored light and sound conditions. In either event, the data accumulated will be stored in the computer for reference throughout the conference. It should be noted, however, that such pre-conference testing should be done prior to each session of teleconferencing, as the individual's brain functioning characteristics can change considerably from time to time.

During the conference the conferee must wear an ear piece which will be suspended on the left ear, and is wired to provide a left temporal feed to the EEG machine, and a soft projection of the synthetic sound previously determined to be most effective. The feed of information to the EEG machine will detect changes in the conferee's brain functioning during the conference, and permit automatic adjustment in the colored light and sounds which may be necessary to assist in maintaining for the conference significant alpha rhythm brain functioning.

In the EEG-computer set-up means is provided for averaging and plotting in a readily visible way for projection on the second television screen a meaningful indication of the level of alpha rhythm brain functioning prevailing at the conference station. This will permit ongoing comparison with the similar plotting of alpha rhythm performance at the remote station. This will provide a meaningful indication as to how the conference is progressing, because general conformance between the two patterns will indicate that conferees at the communicating stations are approaching a "meeting of the minds", whereas the development of substantial non-conformance in the two patterns will indicate that effective communication is breaking down. If such non-conformance is temporary and corrected, the conference can go on, but if the non-conformance persists, this could be a signal that the conference should probably be terminated.

It is believed that the improved telecommunication system herein described can greatly improve the effectiveness of teleconferencing by creating an overal environment closely corresponding with that of a round-the-table conference. The slight inconvenience of wearing an ear piece during the course of the conference should present no problem as the soft sound being generated will have no distracting effect on the conferee. The sound can be as innocuous as the soft sound of surf at a variable and controlled frequency; and this would in no way interfere with the comfortable hearing of what is being said at the communicating conference stations. Similarly, with respect to the varied colors being projected from the overhead and in desk light sources, these would provide no distraction, and in fact, the conferee would probably not be consciously aware of the colors, and possible color changes being projected from the overhead and in desk light sources. It is considered, however, that the controlled light and sound environment stimulating for each conferee an enhancement of alpha rhythm brain functioning, can greatly enhance the effectiveness and productivity in the use of Integrated Services Digital Networks.

Limited publication of the LOGOS concepts has appeared in the Journal of Religion and Psychical Research in articles by Mr. Thompson appearing in JRPR Volume 6, No. 4, October 1983, pages 309 to 312; and JRPR Volume 9, No. 3, July 1986, pages 165 to 174. The first article is directed primarily to the layman, whereas the second article is more scientifically oriented, and relates the LOGOS concepts to the recent work of others in several disciplines.

According to the LOGOS concepts, an understanding of "overall reality" requires the recognition of the existence and significance of the spiritual realms which create and control the material realms with which we are familiar. The spiritual realms involve seven families of spiritual life forms associated respectively with atoms, molecules and inanimate matter generally, plant life, animal life, human life when functioning at the alpha and higher voltage brain wave levels, distant oases of advanced intelligence, and finally, the infinite wisdom and energy of the universe, equating in religious terms to God.

The seven families of spiritual life forms are at different energy levels, and communications between the different levels, and between spiritual realms and material realms, appear to be accomplished via the Tesla electromagnetics operating within the massless charge that pervades all of what we think of as empty space, including the empty space within molecular and atomic structures.

Each of the seven LOGOS families comprise a "collective unconscious" made up of the spirits of presently existing and previously existing entities of their material realm counterparts, whereby accumulated past experience and wisdom can guide present and future actions in the material realm.

Humans, by reason of their physiology and heritage, are members of the animal kingdom, but are uniquely endowed with "free will" or the "power of abstract thought" which sets them apart from other animal species.

As discussed in the above mentioned July 1986 JRPR article:

"Man's power of abstract thought is viewed as the unique gift that endows him with the "image of God". Man has the ability, not shared by other animals, to consciously, or willfully, switch his brain function between various frequency levels, and in so doing to establish communication (not generally perceived at the conscious level) with various life forms of the LOGOS. Indeed, all memory and recall of past experiences and interpersonal relations is believed to be explained by such communication."

"When tuned to the beta level, which occurs during the frequent periods of anxiety, stress, fear, etc., the individual is being influenced largely by his animal instincts and heritage. Much of the trouble and conflict in the mortal realm is due to man's inability or unwillingness to switch out of beta into the alpha and higher voltage brain wave levels. And much of the pain and illness experienced by mankind results from this inability or unwillingness."

"When tuned to the alpha range, the individual is in communication with the accumulated "human" wisdom of the earth environment, and can find guidance in the handling of problems that others have handled and solved.

"When tuned to the theta range, the individual can be in communication with oases of advanced intelligence and, when properly receptive, can assimilate bits of wisdom new to the earth environment. This accounts for the creativity exhibited by many individuals."

In view of what has been discussed above, it becomes understandable that when the improved telecommunication system of the present invention is functioning in the manner intended, and is effectively guiding participating conferees to attain and maintain enhanced alpha rhythm brain functioning during a conference, the progress and outcome of such conference should be greatly enhanced.

As one creates a light and sound environment that reduces beta rhythem brain functioning and enhances alpha rhythm brain functioning, there can also be some stimulation of the individual's level of theta rhythm brain functioning. This can be particularly advantageous to conferences relating to basic research and concepts new to the earth environment. As a special adaptation of the present invention, the planning for and monitoring of such conferences will involve more precise EEG analysis of brain wave patterns and special attention to finding the particular light source and sound source adjustments which will maximize the conferee's theta rhythm brain functioning.

According to the LOGOS concepts communication between spiritual entities, and between the spiritual and material realms is accomplished via the Tesla electromagnetics as holographic patterns in the massless charge that pervades empty space.

Such communications are "pure thought: communications, without linguistic characterization, and as received by an individual, probably in the right hemisphere of the brain (center of the unconscious) are translated or converted to linguistic terms (in the particular language of the individual) and transferred to the left hemisphere of the brain (center of consciousness).

When an individual is thinking at the conscious level, a left hemisphere function accomplished in linguistic terms, he is generating "material thought". This can be comprehended as an experience of decompression of brainwaves in regular time, or memory. At the same time, he is also generating in his 'spiritual' right hemisphere generic "pure thought" which can accomplish direct mind to mind communication. This generation of generic "pure thought" impulses can be comprehended as decompression of brain waves in Real Time and is experienced as imagination. Meanwhile, each hemisphere is attempting to "understand" the thought impuleses originating in the other hemisphere involving an energy which can be comprehended as compression.

When confronted by a particular problem, both hemispheres of the brain become active. The left hemisphere considers the problem in logical, linguistic and materialistic terms normally associated with beta brain functioning; while the right hemisphere is in spiritual communication with the "collective unconscious", a function normally associated with mixed brain functioning predominantly in the alpha rhythm. "Collective unconscious" can be comprehended as the accumulation in tile earth environment of the present and past thoughts of individuals, living or no longer living mortal life, and hence a reservoir of wisdom of the earth environment stored in a dimension where time and space are infinite, and communication with which is an instantaneous Real Time phenomenon.

In these processes the human mind develops memory which is past reference generated by the linguistic, materialistic left hemisphere, and imagination which, by drawing on the stored wisdom of the "collective unconsious", can generate a broader picture providing a future reference.

When the two brain hemispheres are functioning at distinctly different rhythms, i.e., predominantly beta in the left and predominantly alpha in the right hemisphere, there will invariably be a time delay between the decompressive thought impulses generated in one hemisphere and the compressive action of the other hemisphere in attempting to understand such thought impulses. If the time delay is small, it may be of little consequence; but as the time delay increases, a point can eventually be reached when a state of confusion or chaos exists.

In further explanation of this phenomena it must be born in mind that thought communications in the material, linguistic realm are transmitted by sound and light traveling at different speeds in the regular time, which characterizes events in the material, lingjistic realm, and are being accomplished via the left brain hemisphere which tends to be functioning largely at the beta rhythm of brain functioning. In contrast to this the unconscious thought processes of the right brain hemisphere are being accomplished in a Real Time environment, a dimension in which time and space are infinite, and communication is instantly possible with any of the life forms of the LOGOS.

This difference between Regular Time left hemisphere thought processing and Real Time right hemisphere thought processing accounts for the difficulties currently experienced in conferencing situations, and particularly in the use of video telecommunication systems.

According to the present invention these problems can be greatly minimized or overcome by the preconditioning of participating conferees to attain, as closely as possible, a synchronized alpha rhythm functioning in both the left and right brain hemispheres. This is accomplished by the variable light and sound environment in which colored lights and sounds are interrelated in a manner that violet and blue are associated with low sound frequencies, green and yellow are associated with mid-range sound frequencies, and orange and red are associated with high frequency sounds.

In the conferee precondition the colored lights are first flashed in the order violet, blue, green, yellow, orange, red with associated changes in sound frequencies tending to stimulate the right brain hemisphere toward alpha rhythm functioning. The lights are flashed in the reverse order, red, orange, yellow, green, blue, violet with the associated changes in sound frequencies tending to stimulate the left hemisphere toward alpha rhythm functioning.

This alternating exposure to changing light and sound environment is continued until input to the EEG unit reveals that a uniform alpha rhythm functioning has been achieved in at least one brain hemisphere, which will generally be the right hemisphere. The sequence of changing lights and associated sound will then be repeated, a number of times if necessary, for the other brain hemisphere, the sequence being red, orange, yellow, green, blue, violet if it is the left hemisphere that needs further stimulation. A point will eventually be reached when the EEG unit will reveal that the left hemisphere is also functioning at a fairly uniform alpha rhythm, and that the left and right hemisphere functioning are quite similar.

In the ideal situation when both brain hemispheres are functioning in a generally similar way in the alpha range there will be no conflict and time delay, and a "yes" decision concerning the conscious thought can be reached instantly in what can be thought of as a Real Time phenomenon. With the two brain hemispheres thus properly "in tune" the conscious thinking and unconscious thinking are simultaneously reaching the same conclusion.

BRIEF DESCRIPTION OF THE DRAWINGS

Novel features of the improved video telecommunication system of the present invention will be more fully understood from a consideration of the following description, having reference to the accompanying drawings in which various parts and components are identified by suitable reference characters in the several views, and in which.

DETAILED DESCRIPTION OF THE DRAWINGS

Figure 1:
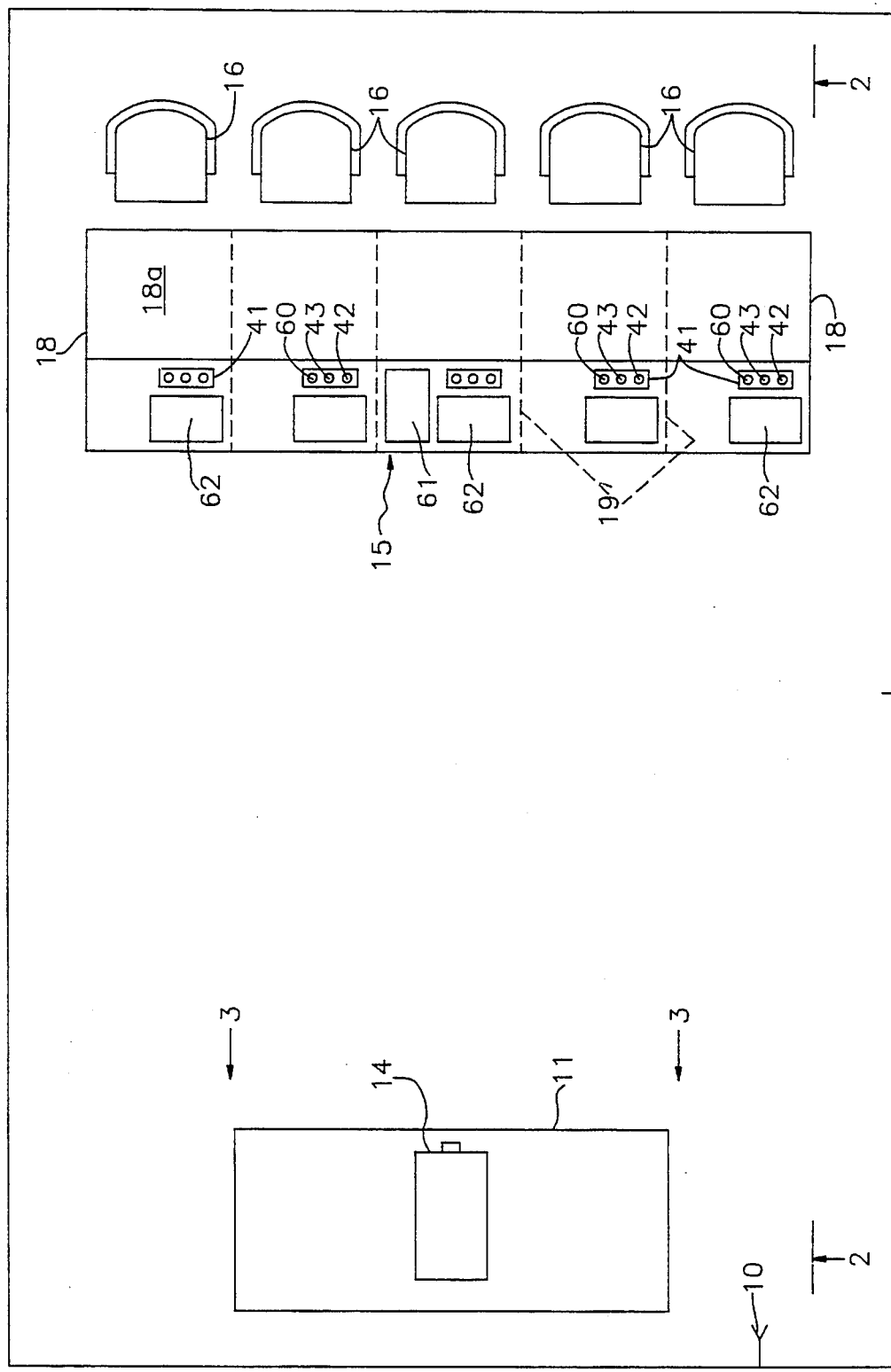
FIG. 1 is a schematic plan view of a conference station incorporating novel features of the present invention.
Figure 2:
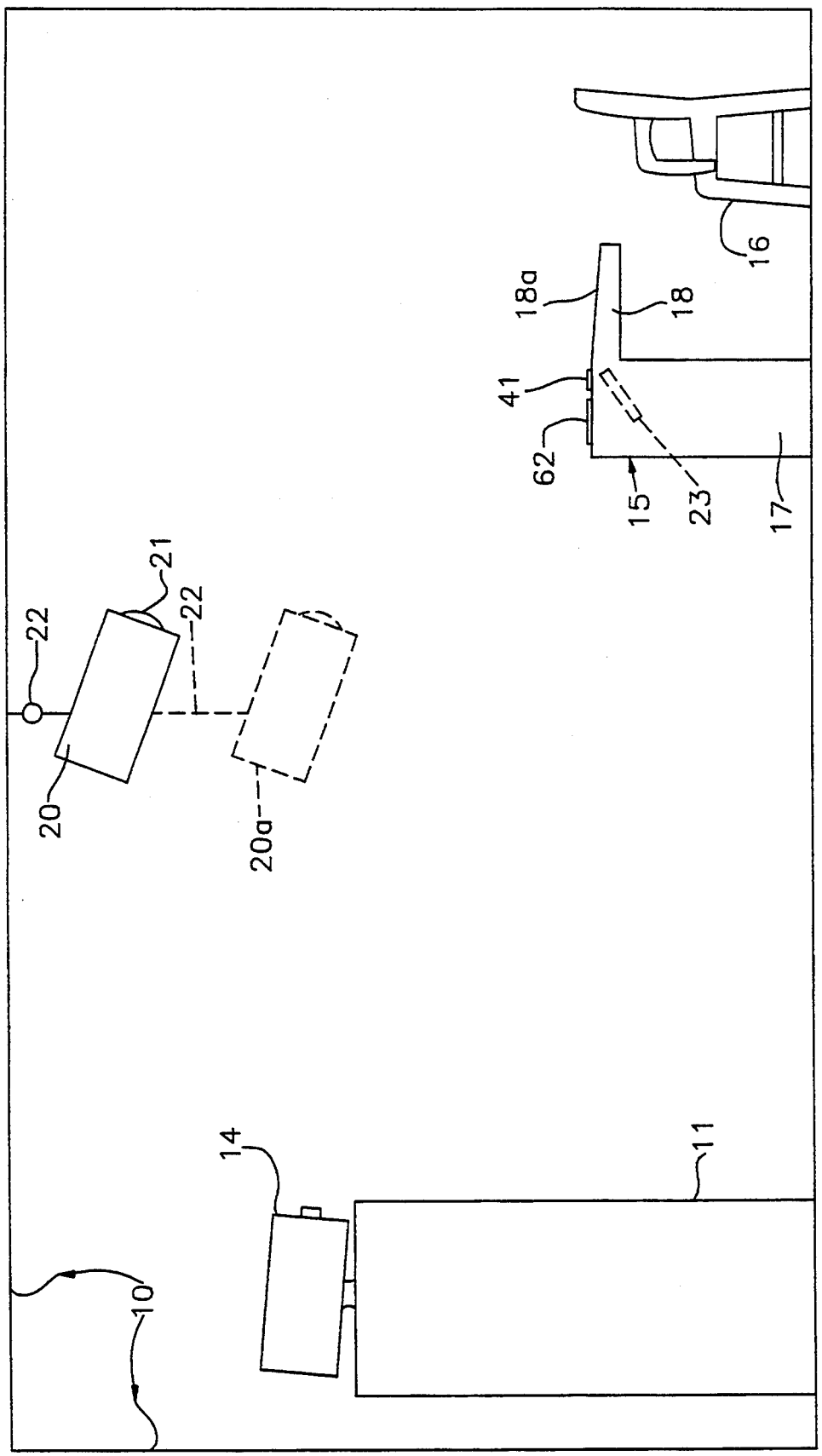
FIG. 2 is an elevation view of the conference set-up of FIG. 1, taken in the direction of the arrows 2,2 in FIG. 1.
Figure 3:
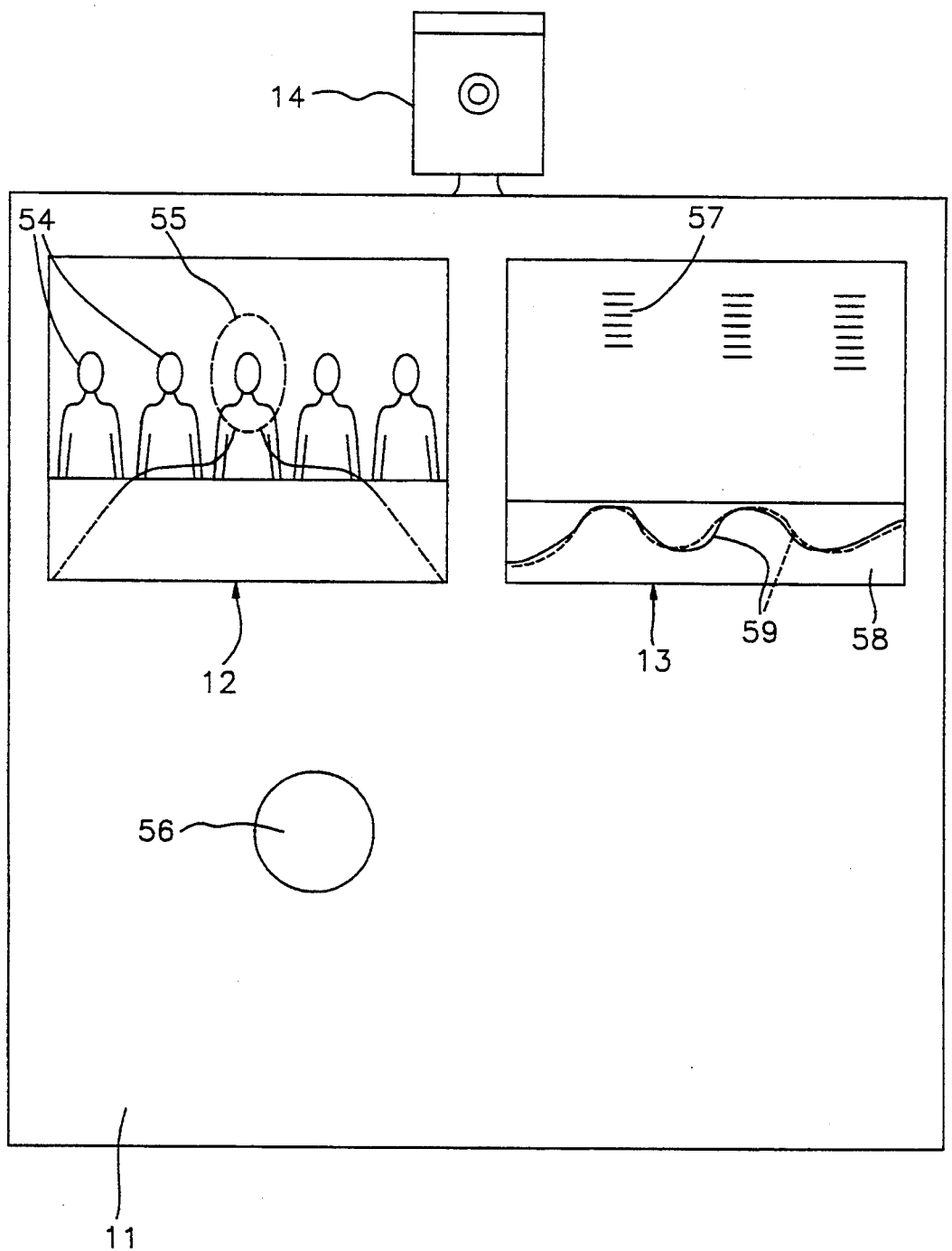
FIG. 3 is a front elevation view of the television screen and camera unit, taken in the direction of the arrows 3,3 in FIG. 1.

As shown in FIGS. 1 and 2 in the drawing, a video telecommunication station, in accordance with the present invention, is housed in a room 10, having at one side a unit 11, positioning dual television screens 12 and 13 as shown in FIG. 3, and a television camera 14. At the other side of the room and generally paralleling the television screen is an elongated work area 15 accommodating a plurality of conferees, five being shown for purpose of illustration, and having independently moving chairs 16. The work area 15 can be a single elongated unit or a plurality of individual conferee units, as indicated by the dotted lines 19 in FIG. 1.

Suspended from the ceiling in alignment with each conferee is an overhead light source 20 having a large lens 21 for properly focusing projected light to the individual conferee. Light sources 20 are mounted on vertically adjustable supports 22 to permit normal storage at the ceiling level and lowering to the dotted line position shown at 20a for conference use. In the lowered position the lights 21a will be close to but not interfering with the line of sight of the television camera 14, as it views conferees seated at the work area 15.

The television camera 14 is of a versatile type, having means for quickly switching between panoramic views of a group of conferees seated at the work area 15, and the projection of enlarged views of individual conferees, the recorded images being transmitted to a remote video telecommunication station; and the camera 14 also incorporating a VCR unit for recording the video and audio signals being projected to the remote station.

The upper surface 18a of the desk portion 18 of the work area will be fashioned from glass or transparent plastic material so that the inclined variable light source 23 housed within the base 17 will impinge upon the head and upper torso of the seated conferee.

Figure 4:
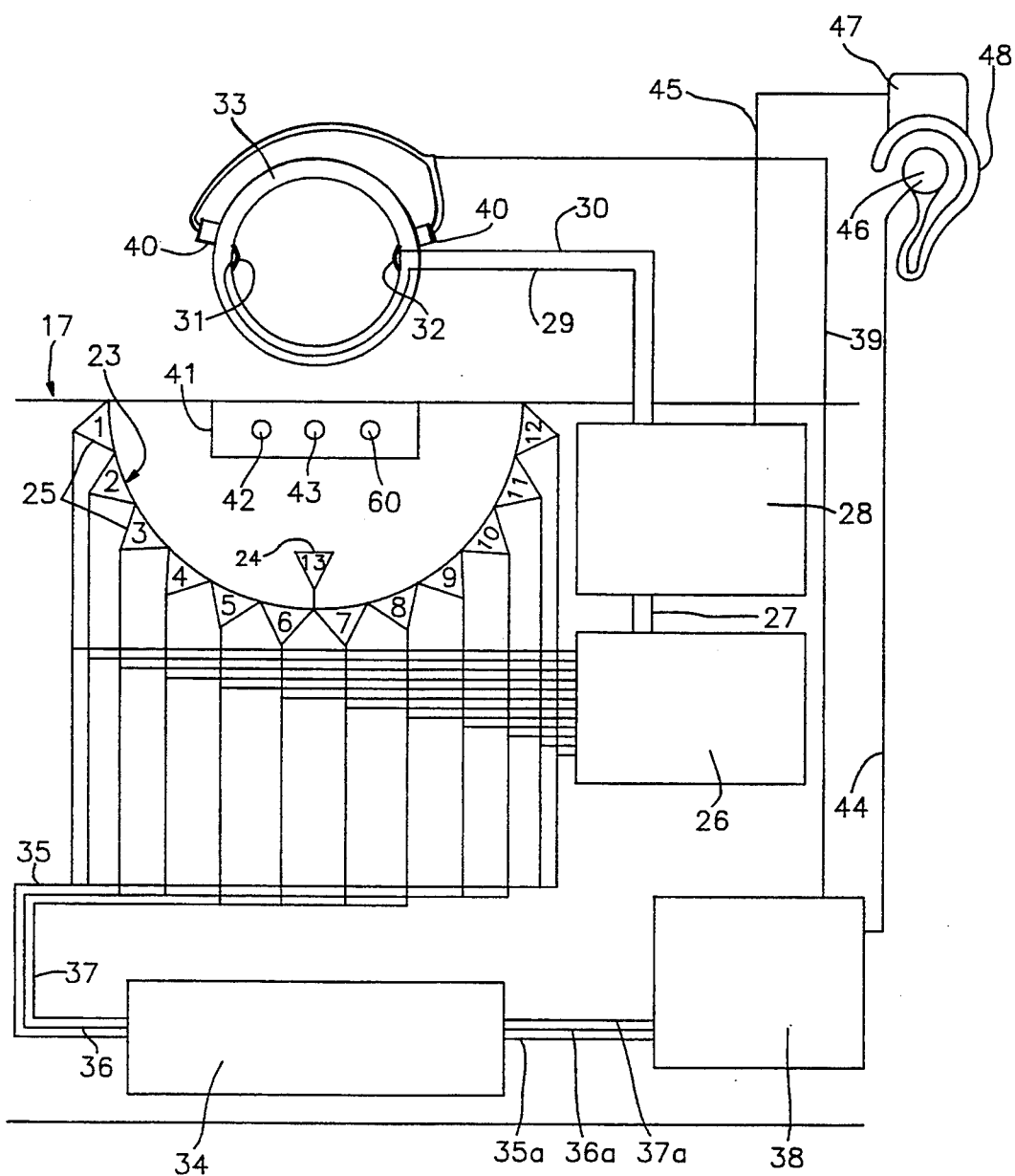
FIG. 4 is a schematic illustration of the variable colored light and sound environmental control utilized by each conferee in preparation for and during a video telecommunication conference.

As shown in FIG. 4 of the drawing, the variable light source 23 incorporates a central white light 24 and an arcuate arrangement of colored lights numbered 1 to 12 in which lights 1 and 12 are violet, 2 and 11 are blue, 3 and 10 are green, 4 and 9 are yellow, 5 and 8 are orange; and 6 and 7 are red.

As shown in the drawing the white light 24, and the 12 colored lights 25 are each linked to computer 26 in circuit as indicated at 27 with EEG unit 28, having leads 29, 30 to temporal probes 31, 32 on an adjustable headband 33, used by the conferees.

The colored lights 25 are joined to light and sound modulator 34 by three separate leads, 35 in circuit with the violet and blue lights, 36 in circuit with the green and yellow lights, and 37 in circuit with the orange and red lights.

At 38 there is shown a variable synthetic sound generator with means for characterizing the generated sounds into three categories of frequency: high, mid-range and low. These frequency ranges are linked with the modulator 34 through lines 35a associating low frequency with the colors violet and blue, 36a associating mid-range frequencies with the colors green and yellow, and 37a associating high frequencies with the colors orange and red. Sounds being emitted by the sound generator 38 are also carried by leads 39 to ear pieces 40 on headband 33.

In pre-conference use of the above described variable light and sound center, a conferee would place the headband 33 on his head and reach for control panel 41 to depress button 42 which activates the pre-conference mode of the equipment. In the pre-conference mode the EEG unit is processing brain wave signals received from the temporal leads 31, 32 and through linkage 27 with the computer 26, alerting the computer as to the relative alpha rhythm functioning in the left and right brain hemispheres.

The object of the pre-conference conditioning of conferees is to achieve both a high level of alpha rhythm functioning, and as close as possible the conformance between the alpha rhythm functioning in the left and right hemispheres. To accomplish this, the computer is programmed to individually illuminate the colored lights in the sequence violet, blue, green, yellow, orange and red to stimulate right brain functioning by simulating the compression which characterizes the right brain energy of converting pure thought impulses to linguistic, materialistic thought impulses. This is followed by a sequential illumination of the colored lights in the order red, orange, yellow, green, blue and violet to stimulate left brain activity by simulating the decompression which characterizes the energies associated with conversion of the linguistic, materialistic thought impulses to pure thought impulses.

As this is happening, the modulator 34 is causing the sound generator to emit synthetic sounds in which frequencies first progress from the low to the high ranges, and then from the high to the low ranges.

As the conferee wearing headband 33 is exposed to the changing light patterns and associated sound changes, the EEG unit 28 will be picking up and feeding to the computer 26, the changes in right and left hemisphere alpha rhythm functioning; and the cycles of changing colored lights are continued until a point is reached when no further increase in alpha rhythm functioning is detected. It will be noted, however, that a peak alpha rhythm functioning will frequently be noted in the right hemisphere before a peak is reached in the left hemisphere, and if the computer encounters such a situation, it is programmed to repeat the light sequence, red, orange, yellow green, blue and violet, several times if necessary, in an effort to bring the alpha rhythm functioning of the left hemisphere as close as possible to that of the right hemisphere.

Based on the number of sequences of colored light changes to achieve substantial conformance between the alpha rhythm functioning of the two brain hemispheres, the computer will select a combination of lights which should be appropriate to maintain that condition, the particular light selection controlling through the modulator 34 the synthetic sound to which the conferee will be exposed. The accuracy of such setting can be confirmed by a uniform EEG response to a few minutes of exposure of the conferee to such setting.

When the light control data has thus been stored in computer 26, the pre-conference mode button 42 is inactivated and conference mode button 43 is activated. This in turn activates sound lead 44 and EEG lead 45 to the speaker 46 and probe 47 respectively on an ear piece 48 which is fitted to the left ear of the conferee. Thus during a conference the conferee will be exposed to the pre-set light and synthetic sound adjustments while the EEG unit is monitoring the left hemisphere for sustained alpha rhythm functioning, so that the computer can appropriately adjust the light and sound setting as needed.

Figure 5:
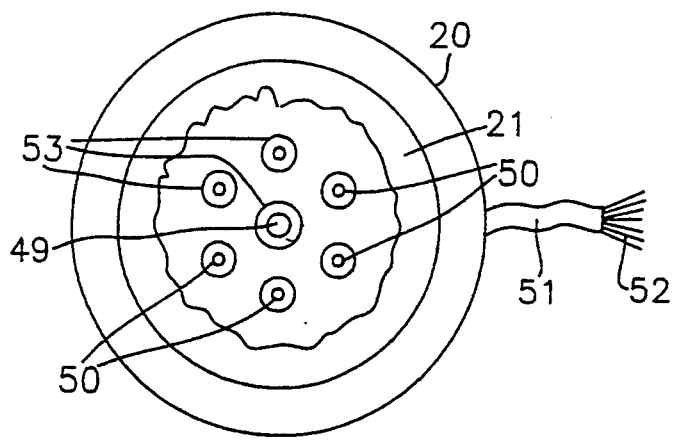
FIG. 5 is a schematic illustration of an overhead light source which integrates with the light control of FIG. 4.

Activation of the conference mode button 43 also activates the overhead light source 20 which, as shown in FIG. 5 contains a central white light 49 closely surrounded by six colored lights 50 in the colors red, orange, yellow, green, blue and violet which are connected through cable 51, having seven leads 52, with the computer 26. Thus, the illumination of colored lights 50 and the colored lights 25 in the work area are synchronized by the computer 26 as to the selection and intensity of colored lights being illuminated. Similarly, the white light 49 and the white light 24 in the work area are synchronized by the computer 26 to provide optimum illumination for camera viewing. It will be noted in this connection that overall illumination of the conferee is provided primarily by the white lights, with the variable colored lights having a physiological impact on the conferee without substantially modifying the overall illumination picked up by the TV camera.

In the overhead light unit 20 reflectors 53 are provided behind each of the lights 49, 50 to assist, in conjunction with the lens 21, in providing essentially uniform overall illumination of the conferee.

Having reference now to FIG. 3 of the drawing, the unit 11 presents, on the surface viewed by the conferees, two large television screens 12 and 13 in close horizontal alignment, and the television camera 14 which, although illustrated as a separate unit, can in practice be housed within the unit 11.

One television screen, 12, will be used primarily for the projection of panoramic views 54 or enlarged individual views 55 of conferees at the remote station, and associated with this television screen as a speaker 56 providing the audio input from the remote station.

The second television screen 13 is divided into a large upper display panel 57, and a smaller lower display panel 58 for graphically displaying comparative brain function patterns 59 of conferees at both stations. Versatile EEG equipment can produce various types of comparative brain function patterns; and by way of illustration equipment produced by Lexicor Medical Technology, Inc., known as NeuroSearch-24 in conjunction with their Biolex System can produce individual and/or averaged wave form patterns or bargraph patterns showing relative degrees of functioning at the different brain wave levels, such as the beta, alpha and theta levels.

During a conference, there will constantly be projected on panel 58 the comparative averaged wave form patterns as generated by the several conferees at Station A and the conferees at Station B; and at times when individual conferees at either station are making extended presentations, there will also be projected on panel 58 the wave form pattern for such conferee.

In this connection, having reference to FIG. 4, a third button 60 on control panel 41 will be activated by the conferee as he embarks on an extended discussion; the activation of button 60 serving to activate the television camera 14 to project an enlarged view of such conferee, and at the same time activate the projection on panel 58 of the wave form pattern of such conferee.

If all conferees at the two communicating stations have been "preconditioned" by the earlier described variable light and sound environment, the averaged brain wave patterns 59 for Station A and remote Station B should show a general conformance, as should the projected pattern 59 for the individual conferee engaged in estended discussion.

So long as these patterns remain in substantial conformance, this is an indication that the conference is progressing favorably toward productive results. If, however, there develops a non-conformance in the projected patterns 59, and such non-conformance persists, this is a sign of breakdown in the negotiating process, and possible lack of productivity in the conference, suggesting the advisability of terminating the conference.

The upper panel 57 on television screen 13 will be used throughout the conference to display various tables, graphs and other visual aids used by conferees at either station and projected on the screens of both conferring stations. For the generation of such images, and having reference to FIG. 1, there is centrally of the work area 15 a transparent panel 61 with a television camera beneath it for viewing the particular visual aids used at the conference.

The upper panel 57 of television screen 13 can also be used from time to time to project computer generated graphics produced by an interaction of the computer-EEG linkage 26, 28 at Station A with the corresponding linkage at Station B.

The software for generating such computer graphics while presently available, but too involved to be included in the present disclosure, is designed to utilize the EEG input of participating conferees at both stations to generate, and constantly modify by response to input variations, the Real Time analysis of the progress of the conference.

These graphics will supplement in a significant way the graphic comparison of conference performance being projected at 59 in lower panel 58, and will enlighten conferees at both stations if and when a true "meeting of the minds" has been reached. In this sense the computer graphics projected on panel 57 supplement the ongoing information and guidance provided in panel 58 by letting the conferees know when a conference can be terminated because its intended goal has been reached. The computer graphics will also provide a clear indication if and when an impasse has been reached, signalling that the conference should be terminated because the conferees have no chance of reaching a "meeting of the minds".

Between these two extremes the computer graphics will provide Real Time indications throughout the conference of shifts between moments of agreement and moments of disagreement, and the trends in frequency of such moments. Meanwhile, the thinking of the individual conferees, through EEG monitoring and adjustment of the individual light and sound sources will be guided to the alpha rhythm brain functioning needed for a successful conference outcome.

While effective computer graphics can be planned and designed in various ways, one approach which is considered to be particularly effective and informative will be briefly described.

Figure 8:
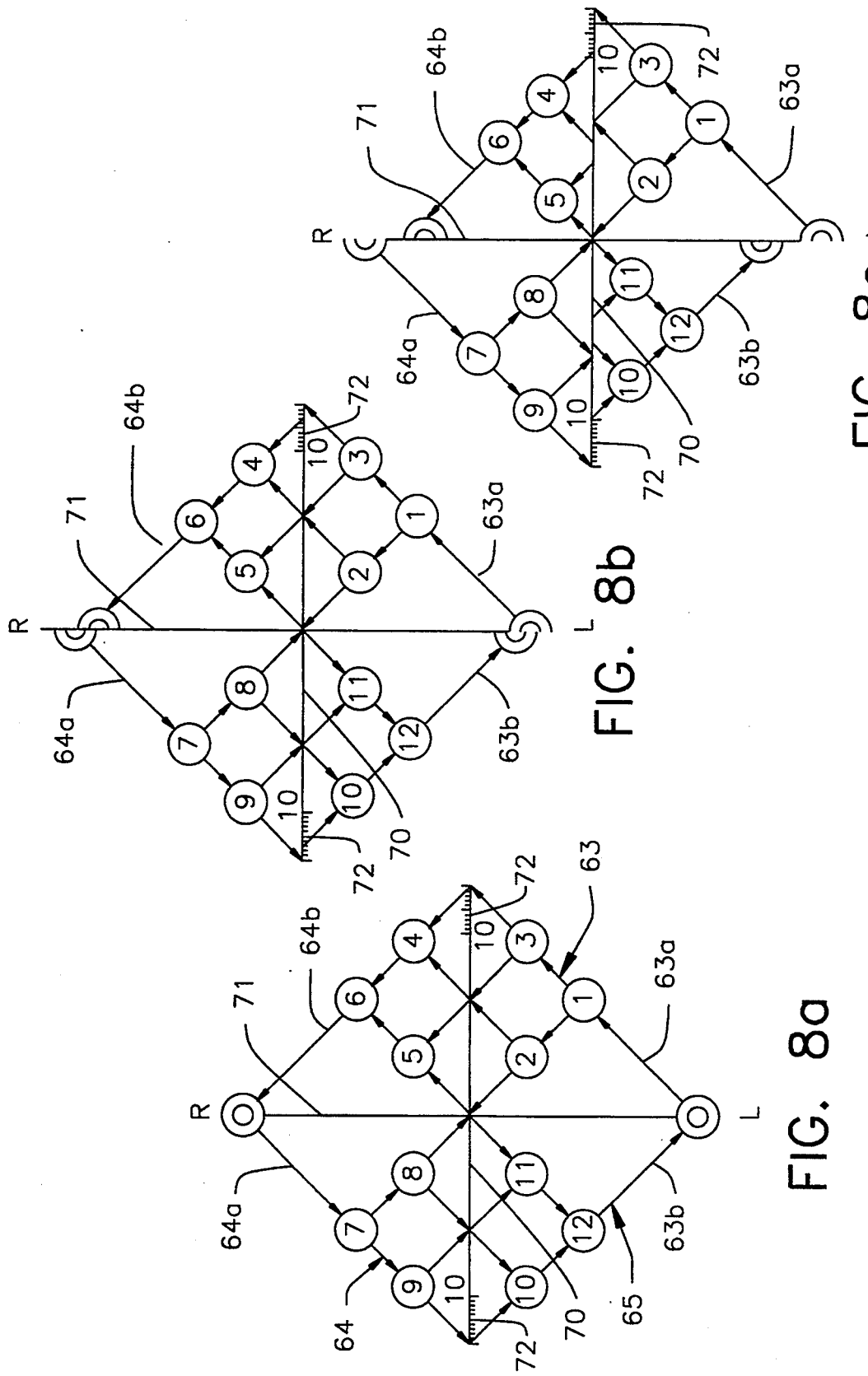
FIGS. 8a–8c are illustrations of typical graphics for projection onto Television screen of FIG. 3.

Having reference to FIG. 8 of the drawing, the computer generated graphics can have the form of two triangles 63, 64 joined at their bases along line 70 to form a square 65. OL and OR represent the confrontation of the left hemisphere of the brain and the right hemisphere, respectively, with a particular question or problem; and the numbered circles 1 to 12 represent the paths of intercommunication between the two hemispheres, with the connecting divergent arrows indicating a function of decompression and the connecting convergent arrow indicating a function of compression.

The numbers 1 to 6 relate to the processing of a thought impulse originating in the left hemisphere and reacted to by the right hemisphere; and the numbers 7 to 12 relate to processing of a thought impulse originating in the right hemisphere, and reacted to by the left hemisphere. It should be noted in this connection that the appearance of the triangles 63, 64 and square 65 in FIG. 8a represents the situation after light and sound conditioning, when the left and right hemispheres have been brought to substantial synchronization at the alpha level.

In addition to horizontal line 70 dividing the square 65 into upper and lower triangles, it has a vertical line 71 dividing the square into left and right triangles and producing, in effect, the four smaller triangles or zones; with zone 63a being conscious decompression, zone 63b being conscious compression, zone 64a being unconscious decompression, and 64b being unconscious compression. Zones 63a and 64a remain unchanged in size, but zones 63b and 64b can vary in size as shown in FIG. 8a, b and c in response to varying EEG input to the computer, being reduced in size in proportion to the reduction of alpha rhythm and increase in beta rhythm in the left brain hemisphere.

At opposite ends of horizontal line 70 are scales or graduations 72 suitably numbering 0 to 10 for visually determining the extent of reduction in zones 63b and 64b. When effectively preconditioned by light and sound to have substantial synchronization between the left and right brain hemispheres, the graphic patterns will appear as in FIG. 8a. As this synchronization is lost, however, and increased beta functioning develops in the left hemisphere, the size of zones 63b and 64b for the individual being monitored, or for a group of individuals as being averaged by the computer, will decrease a small amount as shown in FIG. 8b or a much greater amount as shown in FIG. 8c.

In the FIG. 8a configuration the left hemisphere is in synchronism with the Real Time wisdom of the right hemisphere, and sound or proper answers to problems can be reached instantly. As the regular time thinking of the left hemisphere is increasingly influenced by beta functioning the instantaneous communication is lost, the energy of compression fails to balance the energy of decompression and there is a time delay or error, the extent of which is measured by the scales 72. This error becomes increasingly serious as the zones 63b and 64b decrease in size, and when the point 10 is reached on scales 72, the condition becomes irreversible error or chaos.

When monitoring an individual, as when making an oral presentation, the changes in the graphics can indicate whether his thinking and utterances are sound or flawed, and if so, to what extent. Variations between the patterns shown in FIG. 8a and b would indicate generally satisfactory performance. Occasional deviations approaching the configuration of FIG. 8c would indicate areas of flawed thinking in the presentation, and if such deviations were frequent, or persistent this could be a sign that the entire presentation was flawed.

As applied to use in a video telecommunication systems linking groups of conferees at spaced locations, these graphics can be used in various ways.

One way would be for integration of computers at both stations to average the brain functioning of all conferees and project the composite graphic on the television screens at both stations. This would provide a macro indication as to how a conference was progressing, but would provide no information concerning the relative performance of the two conferring groups.

A more effective approach would be to generate a graphic averaging the brain functioning of conferees at each station and project both graphics on both television screens. In this way it would be apparent to all, which group was providing the more productive input, and which group was creating problems. And if the graphic for either group deteriorated to the FIG. 8c configuration this would be a signal to terminate the conference. On the other hand, if the graphics for both groups are fluctuating between the configurations of FIG. 8a and b, it is a sign that all is going well with the conference.

In an ideal situation, in addition to the two averaged graphics for the conferring groups, there could also be projected on the television screens, the graphic pattern for an individual when making an extended presentation. This would provide a clear indication as to whether the presentation Was being productive or nonproductive.

Figure 6:
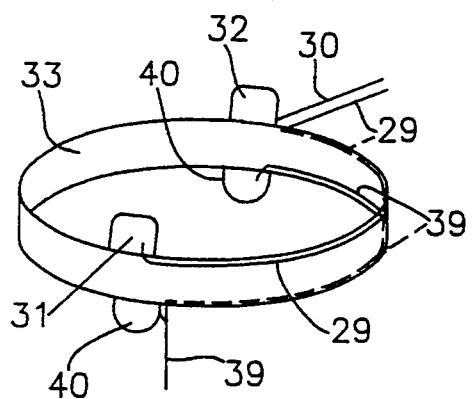
FIG. 6 is a perspective view of the head piece used by a conferee in preconference workup.
Figure 7:
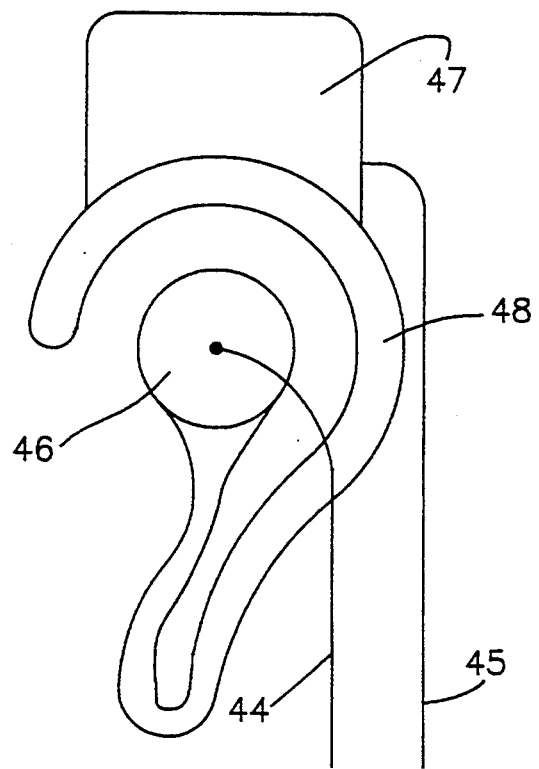
FIG. 7 is a side elevation view of an ear piece used on the left ear of a conferee during a conference.

It will be apparent from the foregoing description that the effectiveness of the improved video telecommunication systems is very much dependent upon the conscientious use by individual conferees of the headband 33 and the ear piece 48 discussed in connection with the description of FIG. 4 of the drawing, and more fully illustrated in FIGS. 6 and 7 respectively. These pieces of equipment, when not in use, are stored within compartment 61 in individual conferee sections of work area 15 which is adjacent the control panel 41 with the previously mentioned control buttons 42, 43 and 60. These buttons, incidentally, will be of the type which illuminate when activated to thereby assist the conferee in their proper use.

In order to further stimulate a round-the-table environment for conferees at remote stations, it could also be desirable to enable conferees at the remote station to have the benefit of an enlarged viewing of a particular conferee who may not be speaking at the time. In such event the control panel 41 would be provided with a row of buttons not shown in the drawing for causing projection on the local television screen of an enlarged view of any selected conferee at the remote station, temporarily superseding any activation of button 60 at the remote station.

While the equipment for creating a variable light and sound environment has been described in FIG. 4 as being provided in each conferee section of work area 15, it should be borne in mind that the system there described could also be set up in a small room or separate rooms apart from the conference station to be utilized by conferees before going into the conference room. Indeed, such an arrangement would be appropriate for the pre-conditioning of conferees planning to participate in a round-the-table conference.

In such a round-the-table adaptation of the invention each conferee would be provided with an overhead light source of the type described and would utilize the ear piece 48 during the course of the conference, and the conference room would be provided with a television screen comparable to the earlier described television screen 13, or possibly two such screens to permit easy viewing by all the conferees. In such a setup the lower panel 58 of the television screen would be projecting brain wave patterns 59 for all participating conferees, with general conformance in such patterns being indicative of favorable progress, and persistent lack of conformance in such patterns indicating lack of progress towards a "meeting of the minds".

Thus it would appear that the heart of the present invention resides in the real time stimulator assemblage, comprising the EEG-computer controlled variable light and sound environment, for preconditioning individual conferees, and for monitoring of brain functioning and adjustment of light and sound environment as needed during the course of the conference, to maintain as much as possible, a uniform alpha rhythm brain functioning among participating conferees.

While in conferencing adaptations of the invention, the provision of means for monitoring brain functioning and adjustment of light and sound environment as needed is of special significance in adapting to varying conditions as different issues may be discussed, it should be noted that the individual preconditioning which is accomplished utilizing the equipment as discussed in describing FIG. 4, can provide further benefits for the individual, notably the health benefits of sustaining brain functioning at the alpha rhythm level as pointed out in the earlier mentioned JRPR publications. Thus an individual having access to equipment such as described in discussing FIG. 4 could utilize the preconditioning function as preparation for normal wakeful activities by approaching a symmetry between tile alpha rhythm function of the left and right hemisphere of his brain.

It would be a simple matter to program the computer, after arriving at the optimum light and sound settings to prepare an audio tape presenting the selective background sound with periodic verbal comment concerning the particular color or hue which the listener should attempt to visualize as an aid in maintaining the synchronized alpha rhythm brain functioning. Provided with such a tape and a small portable cassette player, the individual could, at appropriate times during the day, listen to the tape as an aid in restoring or stimulating his synchronized alpha rhythm brain functioning.

It should be understood that the above mentioned personal use of the variable light and sound approach to attaining real time brain functioning is of but one of several approaches to real time stimulation to be more fully presented in a continuing application. Additional real time stimulators include, inter alia, an adjustable bed, a specially designed chair, a versatile two-way mirror, atmospheric (temperature, humidity and/or scent) control in a closed environment, and generalized light and sound control in a closed environment.

Computer software has been developed to integrate the influence of the several real time stimulators for enhancing the brain functioning of the individual exposed to such stimulators.

It should also be understood that in video teleconconference uses of the present invention there will be fed to the computer facts and data of environmental, economic, medical, social, and/or scientific nature pertinent to the subject matter of a particular conference, with respect to which the normal left hemisphere thinking under the influence of predominantly beta brain functioning may be quite different from the right brain thinking under the influence of predominantly alpha brain function. It is this difference, and the tendency of individuals to act in accordance with their conscious left hemisphere thinking that leads to the difficulty in reaching agreement during conference situations. The light and sound conditioning of conferees can reduce or eliminate this difference and the resulting problems by stimulating left brain functioning toward the alpha level to be in synchronism with the right brain functioning.

Computer software has also been developed whereby assembled facts and data in any particular area, whether it be environmental, economic, medical, social, scientific, etc. will be processed in a way to develop the net real time significance of the accumulated data to thereby enhance the ability of individuals and groups interested in working with data to reach decisions and take actions which will be more productive than decisions and actions based only on rational consideration of past events.

There follows a brief description of the nature of the computer software useful in integrating the beneficial effects of a plurality of real time stimulators and accomplishing the beneficial processing of collected facts and data as above mentioned.

Within the field of computer science known as Artificial Intelligence, scientists are striving to imitate human mental activity and to extend and improve human abilities. One of the claims of Artificial Intelligence researchers is that this work can provide the means for understanding certain mental qualities, such as pleasure and pain. It defines the feeling of pleasure as the degree of positivity, and the feeling of pain as the degree of negativity. It justifies this value judgement by the fact that pleasure is desirable and pain is not.

Artifical Intelligence is therefore based on the assumption that in reality positivity can be increased, and negativity can be decreased. Accordingly, this is an assumption that positivity cannot be increased when negativity is increasing. This is therefore an extension of the rationale behind the statement that there is right and wrong human behavior, and that right behavior must be rewarded and wrong behavior must be punished.

The "reasonableness" of such definition comes from the fact that this is precisely the way that a human being consciously reacts, in relation to the feeling of pleasure or pain, fear or hope, love and hate, and so on. This is contrary to the logic represented by the unconscious human response to pain or stress, however, for it is marked by the pleasurable and extremely healthy release of endorphanes in the brain and neurotransmitters throughout the human body. This release is a fundamental function operating in the human body helping to maintain the immune system and preventing stress, when functioning adequately.

When endorphanes and neurotransmitters are not adequately released in response to painful or stressful events, individuals often use narcotic drugs to temporally decrease stress and nervousness. This substitution of external substances for what the brain provides naturally as stress-pain responses, when too frequently practiced, results in the break down of the natural genetic pathways responsible for the production of endorphins and other neurotransmitters, with a concomitant degeneration in the individual's overall health.

For this one reason Artificial Intelligence will not be able to imitate human mental activities and improve human abilities. All conscious human creative abilities are a manifestation of the unconscious neurotransmitter releases in the brain, a connection that is neglected by "Artificial Intelligence", which rejects pain as an undesirable negativity.

Another highly technical permanent limitation in artificial intelligence is embodied in the algorithm, by which is posited the concept that the general calculational procedure is the same, no matter how large the numbers are: the same finite set of instructions are used, no matter how big the number of recorded data. This is a limitation, since it is evident in the study of "Real Time" that the factor of error in calculational procedure increases as the number of recorded numbers increases. This could be the reason why scientific experts openly admit that neither the activities of neurotransmitters nor the operation of the genetic code is adequately understood.

This is not to say that "artifical intelligence" is useless. It is useful, but only if there is another, "Real Time" computerized model to detect, record and evaluate exactly how pain releases endorphins and neurotransmitters and when this release causes "Real Time" pleasure. This might be different from the human concept of pleasure, since it is a short term effect and is an exact opposite to long-term "Real Time" pleasurable experience.

If "Artificial Intelligence" was regarded as calculational procedure to evaluate short-term effects and "Real Time" as a natural intelligence to calculate long term effects, humanity could develop a computerized method of evaluating reality. Only such a method could become a future reference, which was and still is evaluating short term natural functions.

The "Real Time" computer can be verified by regular-time computer methods such as "Artificial Intelligence". The reason for this verification probability is the fact that regular-time computing evaluates averaged indicators, as real-time computing evaluates non-average. Since all average indicators are derived from non-average functions, one data can be correlated with the other, revealing how two non-average functions cause an average reading on one's instruments.

The existing theoretical description of such a computing method is afforded by what is referred to as quantum computer. Experts in computer science realize that a quantum computer should be possible, but openly admit that they are not yet sure how to actually construct it.

Another limitation is a total avoiding of sexuality which can not be found anywhere in "Artificial Intelligence". It is, therefore, a science to imitate the human mind, an attempt to effect pain and pleasure, but not inluding sex in it. In reality, however, sex controls production of endorphins neuro-transmitters, opiates and other substances experienced as pleasure. The ultimate pleasure is an effect created by the glandular system, releasing sperm or eggs after sexual climax is reached.

People increase their evolutionary advancement when they return sexual energy into their brains, and decrease it when they do not. The experience of pleasure is the return of energy, and stress is when it is not adequately returned. The function of this transmission is to compress brain waves and to compensate for time delay caused by decompression. If this compression process is not adequately carried out, the result is evolutionary regression through degenerative mutation.

The presently increasing sexual harassment, abuse and violence is degenerative mutation reaching point in time when reversible error becomes irreversible. It is a beginning of a general evolutionary regression toward less and less advanced state of life. The unconscious reason is human inability to return sexual energy to it's origin in pituitary gland in the brain which is necessary in surviving future cataclysmic crises created by polluted environment.

The avoidance of sexuality in "Artificial Intelligence" accurately indicates a persistent generally scientific assumption, that it is possible to increase intelligence by decreasing sexual activities.

This is a false assumption because in "Real Time", both, sexual potency and intelligence must increase simultaneously before evolving toward more advanced state of life. The "Real Time" function of sexual potency is to return energy back to its origin in the brain, thus causing intelligence.

Consider that this is precisely the reason why your sex potency is suppressed by this false assumption. This is possible because when you think that sex is unimportant you are actually blocking sexual energy from returning into your brain.

In this way you exchange your "Real Time" intelligence for "Artificial Intelligence" based on a false assumption that development of intelligence is not dependent on a development of higher and higher sexual potency.

When sexual potency is deteriorating more and more people experiment with drugs to increase pleasure and decrease stress. This, however, is a temporary effect and is further blocking return of energy into the brain, thus further deteriorating intelligence axed evolution.

To solve this problem, humanity must develop a software model for a quantum computer programmed to inform, instruct, detect, evaluate and predict sexuality as well as ask and answer most personal sexual questions. The quantum computer is programmed to inform that sexuality is an evolutionary mechanism naturally developed to evolve toward a more advanced state of life. This is why every time people indulge in sexual activities they either increase or decrease their individual and personal evolutionary advancement, depending on their attitude when engaging in sexual activities.

The new approach herein presented involves what may be thought of as "Real Time". Computer hardware, software and graphics designed to detect and correct error created by the fact that different specialized scientific fields are speaking different languages, a factor which limits intercommunication and restricts or prevents the comprehension of totality.

The ultimate function of this new approach is to translate one specialized scientific language into another so that scientists in every field understand the significance of changes in a total system. Existing computerized systems are performing specialized functions, and are not designed to integrate specialized languages.

For example: Presently developing global crises are leading to a conclusion that environmental pollution directly affects genetic structure which is the hereditary mechanism of life. Exactly how this effect is carried out in reality, is not known because scientists in genetic research can not learn from environmental scientists how genetic behavior is affected by pollution.

This is a serious problem since it is a known fact that a polluted environment emanating radioactive nuclear energy can cause degenerative mutation.

A first application of real time software, hardware graphics is to connect genetic science with environmental science through a computerized language revealing how a polluted environment affects genetic structure. The type of software used in this application is known as hierarchical clustering. It is a computerized method to detect and correct error by developing clusters containing smaller and smaller number of members in each cluster.

THE METHOD OF HIERARCHICAL CLUSTERING

Clustering refers to the process of grouping similar objects together. An object could be a description of an entity of interest. The object itself could be a vector of several components (as described in J. Zupan "Clustering of Large Data Sets". Research Studies Press, New York, 1982), or may be a simple element. The similaarity between objects can be represented by a measure of association, which could be either the distance, of n objects, the measure of association among the objects can be represented by an an n * n matrix, where each element in the matrix represents the association between any two objects. Once the similarity matrix is obtained, a method could be devised to use this matrix to generate appropriate groupings.

One trivial solution to the clustering problem is to group the entire set of objects into one cluster. The other extreme is to have n clusters, (n being the number of objects), where each cluster contains exactly one object. Neither of these solutions add to the already existing knowledge about the associations among the objects.

The compactness of a cluster can be represented by the within group variance of any cluster. The more compact the cluster, the less the within group variance. Thus, for the two trivial cases mentioned, the within group of variance of the former is maximum, while that of the latter is minimum among all possible groups.

The purpose of hierarchical clustering is to generate an inverted tree of clusters, where the root is the cluster of all objects, and the leaves are the clusters containing exactly one object, and there are n-2 levels between the root and the leaves. There are measures of errors at each level of the tree, and the problem is to find a method that will generate the tree such that the errors at each level are the minimum for that level.

M. R. Andberg "Cluster Analysis for .Applications". Academic Press, New York, 1973, has categorized the hierarchical clustering methods into linkage methods, centroid methods, and error sum of squares or variance methods. In this section we present four methods, where the single and complete linkage methods belong to the first category, and the Ward's method belongs to the third category. The combined method is a combination of the single linkage, complete linkage, and the Ward's method.

All the four methods presented below are based on the central agglomerative procedure (as described in Andberg), where we start with the clusters containing exactly one object, find the most similar pair of clusters from the similarity matrix, merge the clusters thus obtained, and update the similarity matrix incorporating the effects of the mergers on the other similarity values. In this method the the number of clusters is reduced by one after each step. This process is repeated n-1 times, when the cluster containing all objects is obtained.

The Single Linkage Method

The single linkage method, also called the nearest neighbor approach, updates the similarity between two clusters based on the nearest neighbors. This method tends to generate trees with "long chains" (Zupan, 1982). The following steps are involved in the single linkage method:

From the similarity matrix, find the pair of clusters for which the similarity measure $S_{ij}$ is the most most extreme (minimum for a distance matrix, maximum for a correlation matrix).

Merge the two clusters found in the previous step, and modify the similarity matrix according to the following:

$$\forall k, k \epsilon \{i,j\}, S_{k,r} = extreme\{S_{i,k}, S_{j,k}\},$$

where extreme=minimum for distance matrix, and extreme=maximum for correlation matrix.

Perform the previous two steps for n-1 times.

The Comjplete Linkage Method

The complete linkage method, also called the furthest neighbor approach, updates the similarity matrix after each step in the algorithm, based on the furthest neighbors in the clusters. This method tends to generate inefficient results for "eccentric" or "or "prolongated" clusters (Zupan, 1982). The method consists of the following steps:

From the similarity matrix, find the pair of clusters for which the similarity measure $S_{ij}$ is the most extreme (minimum for a distance matrix, maximum for a correlation matrix).

Merge the two clusters found in the previous step, and modify the similarity matrix according to the following:

$$\forall k, k \epsilon \{i,j\}, S_{k,r} = extreme\{S_{i,k}, S_{j,k}\},$$

where extreme=maximum for distance matrix, and extreme=minimum for correlation matrix.

Perform the previous two steps for n-1 times.

Ward's Method of Hierarchical Clustering

Ward's method is based on the notion of selecting the clusters such that the potential mergers should result in the minimum increase in the within group sum of squares of errors. This method is regarded as very efficient, although it does not always generate the most optimal solutions. Ward's method tends to produce clusters of small groups. In this method, there is no geometrical meaning of the distance between two clusters (Zupan, 1982). The method consists of the following steps:

From the similarity matrix, find the pair of clusters such that their merger would give rise to the minimum increase in the within group sum of square of errors.

Merge the two clusters selected in step 1, and perform step 1 on the resultant group of clusters n-1 times.

The Combined Method

The combined method selects the best group of clusters formed by the three methods described above at each level. The best group corresponds to the one that has the smallest within group sum of square of errors. The method consists of the following steps:

Using the three methods described above, generate three temporary pairs of clusters.

Calculate the within group sum of square of errors for each of the three pairs generated in step 1, and choose the pair with the minimum within group sum of square of errors.

Merge the two clusters selected in step 2, and perform the previous two steps n-1 times.

APPLYING HIERARCHICAL CLUSTERING FOR MEASURING THE IMPACT OF AUDIO-VISUAL STIMULI IN THE GENERATION OF ALPHA RHYTHMS

It is a well established fact that audio-visual stimuli have an impact on the generation of brain waves. We establish empirically the relationship between the audio-visual stimuli and the frequency of alpha rhythms generated. In particular, we establish the combination of light and sound peculiar to the individual that stimulates the generation of alpha rhythms.

Method:

The method consists of a set of light and sound signals that the subject of the experiment is subjected to. The alpha rhythms are picked up by an EEG machine. The light and sound readings that correspond to each of the alpha brainwaves are recorded. The light signals are correlated with the sound signals, and are divided into three frequency rates: low, mid, and high. Once a group of data is gathered, a regression equation can be developed. Let y denote the frequency of alpha rhythms, and $x_1$, $x_2$ denote the frequency range of the light and sound signals respectively. By regressing y on $x_1$ and $x_2$, we get the following.

$$y = \alpha.x_1 + \beta.x_2 + \gamma x_1.x_2,$$

where $\alpha$, $\beta$, $\gamma$ are regression coefficients.

Example;

The previous subsection examplifies how a correlation matrix can be developed that depicts the correlation between any two of the factors used as pollution indicators in the global context and health indicators in the individual context. Suppose there are twelve such indicators: $f_1 \ldots f_{12}$. The correlation matrix is shown in FIG. 1.

where $c_{ij}$, $i = 1 \ldots 11$, and $j = 1 \ldots 12$.

At every stage of the method, the two most similar objects are combined into one object, and the correlation matrix is revised based on the new formation.

Step 1: Find out the minimum $c_{ij}$ in the similarity matrix. FIG. 2 shows the pseudocode that determines the closest elements.

Step 2: Put the closest clusters in one cluster. Suppose $c_{1,6}$ is the maximum in the correlation matrix. This means that $f_1$ and $f_6$ are the two most similar factors. Incorporating this into the correlation matrix would require modifying the correlation matrix. This modification differs from one strategy to another. This is explained in Step 3. The revised matrix is shown in FIG. 2.

Step 3: Update the similarity matrix. The exact method for updating the similarity matrix differs from one strategy to another. FIG. 3 shows two strategies: simple and complete linkage. Basically, the correlation corresponding to the elements that are put in one cluster is calculated by using the centroid of the cluster.

$$\begin{bmatrix}
c_{31} & & & & & \\
c_{31} & c_{32} & & & & \\
c_{41} & c_{42} & c_{43} & & & \\
c_{51} & c_{52} & c_{53} & c_{54} & & \\
c_{61} & c_{62} & c_{63} & c_{64} & c_{65} & \\
c_{71} & c_{72} & c_{73} & c_{74} & c_{75} & c_{76}
\end{bmatrix}$$

$$\begin{bmatrix}
c_{81} & c_{82} & c_{83} & c_{84} & c_{85} & c_{86} & c_{87} & & & & \\
c_{91} & c_{92} & c_{93} & c_{94} & c_{95} & c_{96} & c_{97} & c_{98} & & & \\
c_{101} & c_{102} & c_{103} & c_{104} & c_{105} & c_{106} & c_{107} & c_{108} & c_{109} & & \\
c_{111} & c_{112} & c_{113} & c_{114} & c_{115} & c_{116} & c_{117} & c_{118} & c_{119} & c_{1110} & \\
c_{121} & c_{122} & c_{123} & c_{124} & c_{125} & c_{126} & c_{127} & c_{128} & c_{129} & c_{1210} & c_{1211}
\end{bmatrix}$$

FIG. 1: Lower Triangular Similarity Matrix

```
begin {Finding the closest clusters.}
    Temp = MAXINT
    for i = 2 to Number of Elements in the matrix do
        for j = 1 to i-1 do
            if (Temp > c_{i,j}
                begin
                    Temp = c_{i,j}
                end; {if}
    Closest = c_{i,j}
```

FIG. 2: Finding the closest elements $$\begin{bmatrix}
c_{32} & & & & \\
c_{42} & c_{43} & & & \\
c_{52} & c_{53} & c_{54} & & \\
c_{[1.6]2} & c_{[1.6]3} & c_{[1.6]4} & c_{[1.6]5} & \\
c_{72} & c_{73} & c_{74} & c_{75} & c_{7[1.6]}
\end{bmatrix}$$

|     |     |     |     |        |     |     |     |      |      |
|-----|-----|-----|-----|--------|-----|-----|-----|------|------|
| $c_{82}$ | $c_{83}$ | $c_{84}$ | $c_{85}$ | $c_{8[1.6]}$ | $c_{87}$ | | | | |
| $c_{92}$ | $c_{93}$ | $c_{94}$ | $c_{95}$ | $c_{9[1.6]}$ | $c_{97}$ | $c_{98}$ | | | |
| $c_{102}$ | $c_{103}$ | $c_{104}$ | $c_{105}$ | $c_{106}$ | $c_{107}$ | $c_{108}$ | $c_{109}$ | | |
| $c_{112}$ | $c_{113}$ | $c_{114}$ | $c_{115}$ | $c_{117}$ | $c_{118}$ | $c_{119}$ | $c_{1110}$ | | |
| $c_{122}$ | $c_{123}$ | $c_{124}$ | $c_{125}$ | $c_{12[1.6]}$ | $c_{127}$ | $c_{128}$ | $c_{129}$ | $c_{1210}$ | $c_{1211}$ |

FIG. 3: Lower Triangular Similarity Matrix after Combining Clusters 6 and 1

```
begin {Extreme}
        RowGroup = Group in which Row belongs;
        ColGroup = Group in which Col belongs;
        case Choice of
            Single:begin
            Temp = MAXINT;
            for i = 1 to NumberOfElements do
                for j = 1 to NumberOfElements do
                    if(i in RowGroup) and (j in ColGroup) then
                        if(Temp > c_MoreOf(i,j).LessOf(i,j)
                        then Temp = c_MoreOf(i,j).LessOF(i,j)i
        end; {Single}
        Complete :begin
                    Temp = -MAXINT;
                    for i = 1 to NumberOfElements do
                        for j = 1 to NumberOfElements do
                            if (i in RowGroup) and (j in ColGroup) then
                                if (Temp > c_MoreOf(i,j).LessOf(i,j)
                                then Temp = c_MoreOf(i,j).LessOf(i,j)i
        end; {Complete}
        end; {case}
        Extreme = Temp;
end; {Extreme}
begin {ModifySimilarityMatrix}
        for i = 2 to NumberOfElements do
            for j = 1 to i-1 do
                if i and j being to the same group then
                    case Choice of
                        Single: c_{i,j} = MAXINT;
                        Complete: c_{i,j} = -MAXINT;
                    en {case}
                else c_{ij}[i,j] =
                    Extreme(i,j,NumberOfElements,Group,c_{ij},Choice);
end; {ModifySimilarityMatrix}
```
FIG. 4: Modifying Similarity Matrix A first stage in this application is development of a generic software model for global pollution control necessary in gathering a global pollution data. After gathering the global data the real time computer base will correlate environmental information through hierarchical clustering aimed at detecting and correcting error.

A second stage in this application is to correlate environmental data with genetic data to discover exactly when environmental pollution causes genetic degeneration. It is already evident that particle of aluminum inside gene 19 is causing death or brain cells causing unprecedented acceleration of aging and death.

Prior art in genetic research is limited only to detecting the sequential arrangement of genes but not the relationship between them. The present approach is designed to translate this arrangaement and reveal the relationship between them. This is necessary in comprehending how sequential arrangement is naturally implemented. The present approach, therefore, is designed to link different areas of prior art and achieve a computerized and comprehensive method to investigate a total system.

It is important at this point to present a brief explanation or definition of what is meant by "Real Time".

Time is now transforming regular into real time. Regular time can be comprehended as past reference and real time as future reference. Real time is a mirror image of regular time-similar, but radically different.

The fundamental difference is that in the past in regular time, larger causes created smaller effects; whereas in the future, in real time, the opposite will take place; smaller causes will create greater and greater effects.

For example, $E = MC^2$ is a past reference in regular time stating that energy equal matter measured as weight, and multiplied by the never-changing speed of light. On the other hand, $qp-pq = ih/2\pi$ is a future reference in real time, stating that the speed of light is changing when the intensity of light changes.

Max Planck was the world-renowned scientist who discovered real time. He called it the Quantum Law, stating that $qp-pq = ih/2\pi$. This means that when dispersing energy waves transform into gathering waves, the result is a photon, identified as Planck's Constant, and mathematically written as $6.55 \times 10^{-27}$ ERG-SECONDS.

The meaning of these numbers has to do with a fact that in reality there are two types of energy waves, expressed in terms of intensity (ERG) and time (SECONDS). This means that there are some waves for which intensity increases when their time decreases, and other waves for which intensity decreases when the time increases.

This is why $6.55 \times 10^{-27}$ ERG-SECONDS is a product of two other numbers: one representing intensity of energy, in ERGS, and the other the period in time during which this energy is released, in seconds. Scientists who developed these numbers realized that one number can increase when the other is decreasing. For example: they discovered that when the period in time is decreasing, the intensity is increasing. This is why matter is in a constant explosive state caused when decreasing periods in time are releasing increasing amounts of nuclear energy.

Planck wrote in "The Philosophy of Physics" (page 115) "Thus we observe, what we have already observed on several occasions, that there is an irrational core at the center of science which no intelligence can solve, and which no modern attempt at limiting the definition of the task of science can remove . . . "

Today we can comprehend that the "irrational core at the center of science" was brought about by natural resistance in the past to accept future reference in real time. This manifested an unwillingness by scientists to accept the postulate that smaller causes can create larger effects, which they considered an impossibility. They believed that only larger causes can create smaller effects because energy is always lost through decompression during this process.

However, according to quantum real time law, energy, during the process, can be compressed and decompressed and instead of energy loss, there can be energy gain, written as: $ih/2\pi$.

The energy gains its intensity when the compression of energy waves compensates for the time delay caused by decompression, thus causing instantaneous causes and effects on many levels simultaneously.

Today in the fiber optic research, scientists have discovered what they call "solitan pulses" transmitting 100 billion bits of information per second. This can be comprehended as an instantaneous energy transmission which is transmitting many different signals of information. The "solitan pulse" can be comprehended as $ih/2\pi$ transmitting information in Real Time.

One possible conclusion is that real time, which can be mathematically identified as $qp-pq=ih/2\pi$, can be comprehended as compression and as decompression of energy waves. When qp and pq becomes equal, compression compensates for time delay caused by decompression. Thus $qp-pq-ih/2\pi$.

The implications of this conclusion are literally unbelievable, suggesting the possibility that real time could destroy civilization for a long time, if not forever. When small causes create relatively larger effects they can begin an irreversible chaos on an atomic, molecular, cellular and multi-cellular levels in all living organisms on earth. This can stimulate the accelerated release of nuclear energy from the sub-atomic level, which can deteriorate genetic structure, causing accelerated degenerative mutation.

There are at least two different causes of degenerative mutation.

1. The natural planetary evolution, triggering a predominance of compression to compensate for energy loss and time delay, caused by decompression.

2. The planetary pollution which is accelerating natural evolution, and obstructing the return of compression back into decompression, thus causing an explosive state all over the world simultaneously.

Max Planck has stated in *Philosophy of Physics*, Page 113: "In my opinion the only possible method available here is that which we followed when dealing with optics, a method applicable not only to physics, but to every department of science, and we do this when we remember that every science requires some person to build it up and to communicate it to others. And this means once again the introduction of the principle of totality."

Totality is difficult to comprehend, but a computerized method to integrate all the various departments in science is possible, if it is based on $qp-pq=ih/2\pi$.

Figure 9:
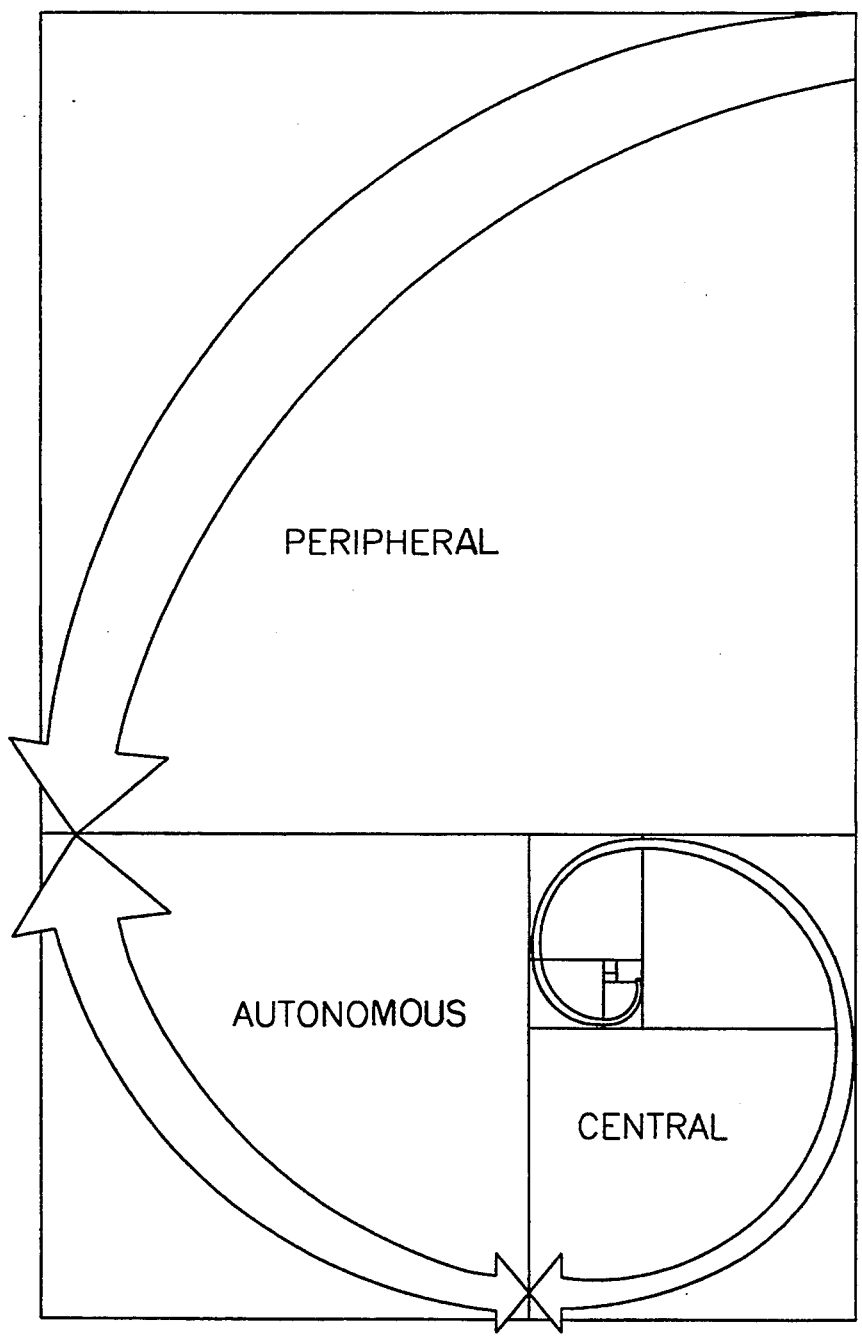
FIG. 9 is a graphic illustration of the relation of control, peripheral and autonomous phenomena.

The "Real Time" logic is radically different from linear and infinite regular time because "real Time" is a sequential cyclic process, and therefore can be expressed in a spiral arrangement (See FIG. 9).

The fundamental meaning of the spiral shows that it is a repetitious arrangement of three molecules, performing (1) perppheral (2) autonomous and (3) central functions. The peripheral function is to send energy into the center and central function is to send energy into the peripheral, thus exchanging energy flow.

Autonomous function is to coordinate this exchange so that the amount of energy in the center is balanced with the energy in periphery. When this energy is not coordinated, the molecule performing autonomous function enters state of error which disrupts the sequential molecular arrangement.

The error is created by autonomous malfunction resulting in polarization between central and peripheral molecules. This error in one autonomous molecule is simultaneously spreading to other molecules performing central and peripheral functions, thus instantaneously accelerating a polarization process. This process can also polarize other molecules in their central, autonomous and peripheral arrangements. In this way spreading error from one molecule is transmitted to another and reaching a point in time when reversible error becomes irreversible. This polarization is an unprecedented development, not previously recognized in recorded history, but possibly accounting for the collapse of ancient civilizations.

In extreme cases it manifests more and more often as a determination of the mind to literally kilt the body. The natural reason is molecular polarization between molecules performing central, autonomous and peripheral functions. For this reason the first function of "Real Time" software is to detect and simultaneously postpone the point in time when reversible error becomes irreversible.

This detection is carried out by electro-encephalogram or other biofeedback devices. The postponement is carried out by the computer programmed to operate various "Real Time" stimulators functioning as stimulators of Alpha Rhythm.

Following this logic the computer is programmed to inform the user about the point in time when he or she is reaching irreversible error while simultaneously decreasing the error through comprehensive communication and the use of six "Real Time" stimulators. The function of stimulators is to increase Alpha Rhythm which is accepted by computer logic as indicating correction of error.

Figure 10:
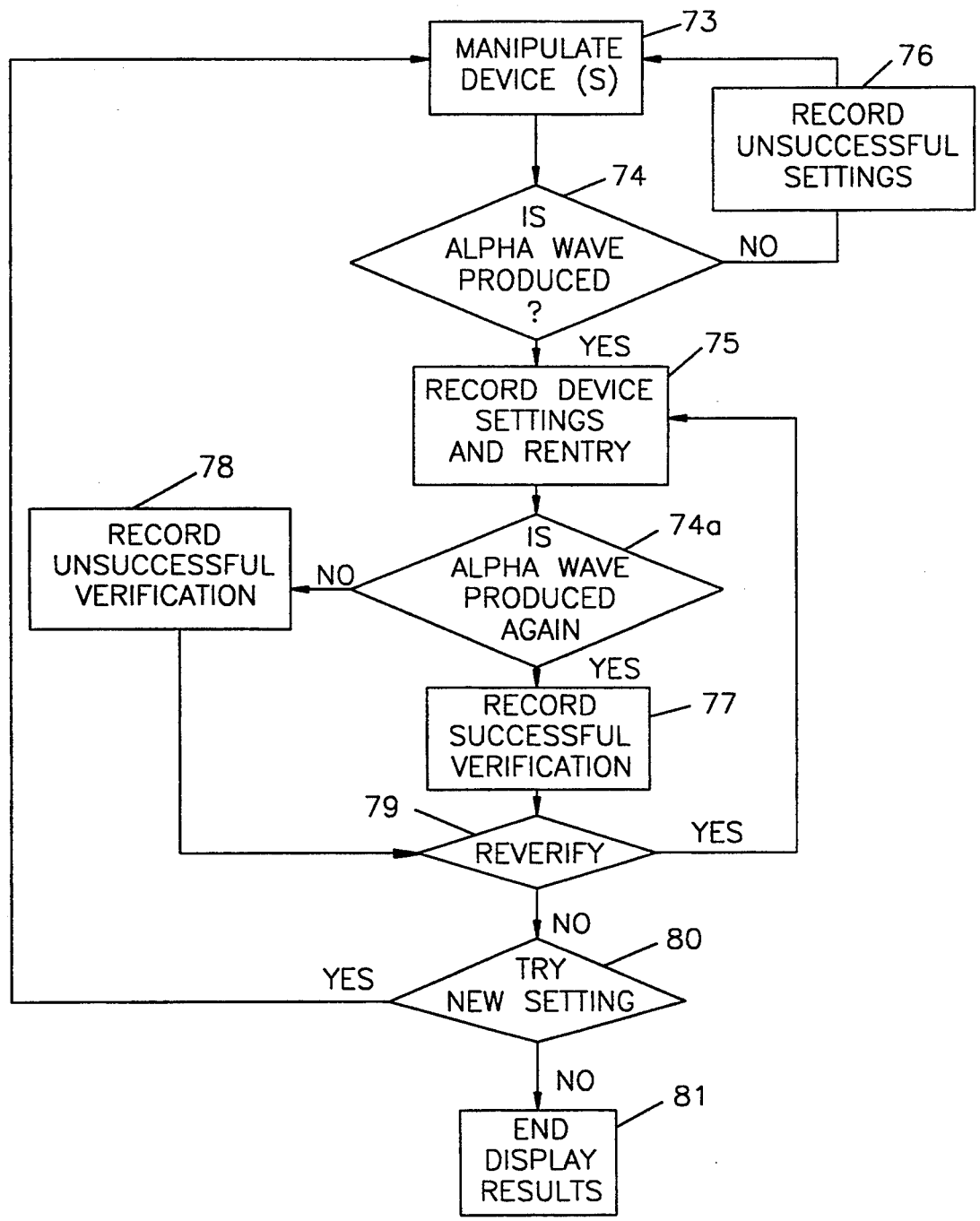
FIG. 10 is a flow chart of a computerized method of utilizing "Real Time" stimulators.

The flow chart of FIG. 10 represents the computerized method for detecting, recording and evaluating the effectiveness of a "Real Time" stimulator, which is a device or combination of interrelated devices with adjustable features having varied effect on brain functioning, and the potential when appropriately adjusted to stimulate Alpha Rhythm brain functioning, i.e. in the range of 8 to 12 cycles per second.

As the stimulator(s) is (are) manipulated, as indicated at 73, the subject is wearing a headband with probes connected to an alpha wave detector 74. The alpha wave detector will either pass on to computer 75 the nature of the Alpha Rhythm detected, thereby signalling the computer 75 to records the settings of the stimulator(s), or failing to detect Alpha Rhythms, will record the unsuccessful settings as indicated at 76, and will signal to vary the settings of the stimulator(s).

After recording successful Alpha Rhythm producing settings, a verifying cycle is started in which the previously successful settings of the stimulator(s) are reproduced, with the alpha wave detector determing, as indicated at 74a, whether or not Alpha Rhythm is again produced. Successful verification is recorded at 77 and unsuccessful at 78. These recorded results can be reverified as many times as desired, as indicated at 79. A decision is then made to try for different stimulator settings as indicated at 80, if the results of reverification have been poor; or, if results of reverification have been good, to end the process and display results as indicated at 81.

It will be apparent that this method, particularly when incorporating the herein discussed technique of hierarchical clustering in the processing of a quantity of recorded data, will permit the manipulation of any "Real Time" stimulator to guide the subject under test to the desired level of Alpha Rhythm brain functioning.

Consider hierarchical clustering in "Real Time" as the direct opposite to artificial intelligence designed to work in regular time. Consider "Real Time" as natural intelligence and non-rational reasoning developed to decrease polarization of natural systems and postponing the point in time when reversible error becomes irreversible.

The ultimate function of "Real Time" generic software is to minimize, and in time eliminate all limitation now effecting artifical intelligence through hierarchical clustering which functions to correct logical reasoning. Consider regular time as backward and "Real Time" a forward reasoning. Consider backward as statistical accounting of average data in a group of individuals, and forward as not statistical accounting of non-average data in a single individual.

Accordingly, the ultimate function of "Real Time" software is to develop quantum super computer capable to compute regular and "Real Time" simultaneously. Consider regular time as short term, and "Real Time" as long term computation of similar natural phenomena.

For example: Life expectancy in regular time indirectly derived from statistical accounting of health symptoms in a group in the attempt to evaluate individual health can be comprehended as a study of short time effects.

Therefore, the lengthening of life span might not be a temporary short term effect created by an exchange of natural vitality for longevity. To verify this possibility a "Real Time" quantum computer could be used to directly detect individual health.

In "Philosophy of Physics" the regular time is identified as Classical Concept and "Real Time" as Quantum Concept. The present software invention can therefore be comprehended as linking these two controversial concepts. This is important since now the controversial meaning between these two concepts is obstructing further scientific progress.

The computerized linkage of classical and quantum concepts could also link the conscious with the unconscious. Since conscious is functioning in regular time and unconscious in "Real Time" this linkage is possible and it should achieve desparately needed unification in science.

The function of this logic is to unify the state of individual health with the state of natural environment and to correlate observed individual and environmental changes.

In one application hierarchical clustering correlates environmental pollution data with individual brainwaves data. In the first stage the purpose is to detect the effect of environmental pollution on brainwaves. In a second stage the purpose is to detect the effect of environmental pollution on the genetic structure.

The ultimate achievement of classical and quantum linkage might result in scientific definition of the free will mathematically identified as quantum jump $qp-pq=ih/2\pi$. Consider quantum jump as a result of interaction between conscious regular time and unconscious "Real Time" activity. Consider quantum jump as a product of symmetrical algorithm when compression of energy waves compensate for time delay caused by decompression.

The free will can therefore be comprehended as instantaneous response to environmental changes in "Real Time". It is therefore possible that the inability to exercise free will is caused by delay in time between causes and effects.

In addition to linking fundamental scientific concepts the present invention comprises a simulated model identified as "Real Time" Environment. It comprises six novel "Real Time" stimulators, computer and electroencephalogram. The purpose is to provide a second verification method implemented through the use of computerized hardware. The first verification is provided by software linking fundamental scientific concepts. The purpose of these two verification methods is to verify every assumption and simultaneously decrease time delay between realization of danger and finding realistic solution.

Software verification of scientific concepts will also provide a new method to verify reasoning. This is achieved when forward verifies backward reasoning. Consider classical concept as backward reasoning since it is evaluation of individual health indirectly reached through statistical analysis expressed in average data in regular time.

Consider quantum concept as in "Real Time" forward reasoning, since it is direct evaluation of individual health, directly through individual and personal non-average indicator such as brainwaves reflexes and other unconscious functions.

This verification should not be mistaken for what is now known as computerized prediction of the past. This is a method to synthesize in the present natural condition which existed in the past and compare it with hisitorical evidence in the attempt to verify computer synthesis.

A proper identification for this method is verification of past references. This is in sharp contrast to "Real Time" verification of regular time which can be identified as future reference.

Consider that only future reference can accurately predict the future which is now becoming quite different from the past. The natural reason is the evolutionary transformation of decompression into compression necessary in maintaining "Real Time" communication between the environment and the individual. For this reason humanity in order to survive must develop a computerized method to evaluate the future when smaller and smaller causes create larger and larger effects.

In closing the reader is again reminded of the LOGOS concepts as discussed in the earlier mentioned October 1983 and July 1986 publications in the Journal of Religion and Psychical Research. According to the LOGOS concepts man, by reason of his "free will" or power of abstract thought, can communicate (subconsciously) with, and be guided by, several collective unconsciouses, each at different energy levels.

When functioning primarily at the beta brain wave level, man is in communication with and guided by the "animal" collective unconscious. In so doing he is greatly influenced by attitudes of anxiety, greed, aggressiveness, hostility and fear which were essential to the survival of many of our animal forbears.

When functioning significantly at the alpha brain wave level, man is in communication with and guided by a higher energy level, alpha oriented, collective unconscious in which animal instincts are put aside, and the guiding attitudes are love, concern for others, and respect for the environment.

It stands to reason, therefore, that a computerized system for assisting man in attaining synchronized alpha rhythm brain functioning is his two brain hemispheres must function more effectively in interpersonal relationships, conferences, etc., and to more clearly understand and better deal with problems confronting present day civilization; and in so doing help to prevent the irreversible chaos which threatens to destroy our civilization, as others have been destroyed in the past.

Various changes and modifications in the method and means for enhancing the productivity of video telecommunication systems and round-the-table conferences, as well as providing supplemental benefits to participating individuals through the EEG-computer processing of a variable light and sound environment as herein described may occur to those versed in the art; and to the extent that such changes and modifications are embraced by the appended claims, it is understood that they constitute part of the present invention.

I claim:

1. An improvement in video, telecommunication systems wherein geographically spaced conference stations are interconnected by telephone, television and computer lines enabling such systems to be more productive by functioning on an essentially real time basis, said improvement comprising the provision at each conference station of:
    a. television screen means arranged at one end of the conference station,
    b. at least one work area at the opposite end of the conference station, each comprising a desk housing,
    c. versatile television camera means including means for quickly switching between an adjustment for panoramic viewing of a group of conferees, and separate enlarged viewing of individual conferees, said camera means including means for projecting a signal to the remote conference station,
    d. means for illumination of the occupants of the work areas including a plurality of variable light source means aimed at respective ones of said work areas for illumination of the occupant thereof, with each light source containing individually variable white light and red, orange, yellow, green, blue and violet light sources,
    e. electronic equipment means, said electronic equipment means including versatile EEG facility means for monitoring brain functioning of the conferees, a variable synthetic sound generator and modulator means for correlating ranges of frequencies of the output of said variable synthetic sound generator with corresponding color lights of said means for illumination,
    f. a compartment at each work area housing:
        (1) a head set for pre-conference use in selecting optimum light and sound adjustment for the occupant, providing left and right temporal EEG leads and an ear piece coupled with the variable sound generator, and
        (2) a small ear suspended unit for in-conference use on the left ear providing a left temporal EEG lead and linkage to the variable sound generator,
    g. a versatile computer interconnecting with the EEG inputs and variable light sources for each work area, and with the television screens and television camera means, and with the remote conference station, and
    h. each work area having a control panel including inter alia:
        (1) a first button to be activated during pre-conference mode, and
        (2) a second button to be activated during the conference mode,
    respective desk housings adapted to accommodate participating conferees in each conference station prior to the beginning of a conference, a respective conferee positioning the head set for pre-conference use at his work station on his head, said EEG leads connected to said versatile computer whereby said versatile computer monitors the brain functioning of the conferee when the conferee activates said first button, said computer operably connected to said means for illumination and said variable synthetic sound generator, whereupon when the conferee activates said first button, said computer, responsive to the detected brain functioning of the conferee, adjusts said means for illumination and said variable synthetic sound generator so as to stimulate the conferee until the conferee achieves both a high level of alpha rhythm functioning, and as close as possible, a conformance between the alpha rhythm functioning in the left and right hemispheres of the conferee's brain, all as monitored by said versatile computer, said versatile computer recording for subsequent conference use the necessary data including those adjustments of said means for illumination and said variable synthetic sound generator necessary to achieve the high level of alpha rhythm functioning and the closest possible conformance between the alpha rhythm functioning in the left and right hemispheres,
    said conferee during said conference mode with said small ear suspended unit positioned on the left ear and said second button activated, enabling said versatile computer through said left temporal EEG lead to monitor the brain functioning of the left hemisphere of the individual conferee, said versatile computer comparing the brain functioning EEG readings during the conference to the recorded data stored therein based upon the pre-conference readings to thereafter adjust said means for illumination and said variable synthetic sound generator as necessary to achieve as close as possible the previously determined alpha rhythm functioning level established prior to the conference, said television screen means providing the multiple functions of:
(1) during pre-conference mode, displaying for individual conferees, graphics and data meaningful in the pre-conference adjustment of light and sound sources, and
(2) during conference mode, displaying on one screen interchangable panoramic views and enlarged individual views of conferees at the remote station, and on the other a divided projection displaying at the top the visual aids as used by both stations, and in a small lower section a running graphic comparison of the level of alpha rhythm brain functioning of conferees at both stations, whereby the improved system, when functioning as intended, is assuring enhanced conference productivity so long as the projected alpha rhythm patterns of both stations are in substantial conformance, and indicating a breakdown in conference productivity if the projected alpha rhythm patterns assume and maintain non-conforming configurations.

2. The improvement in the video telecommunication system as defined in claim 1, wherein said versatile EEG facility means includes separate EEG units at each work area.

3. The improvement in the video telecommunication system as defined in claim 1, wherein said versatile EEG facility means includes a single versatile EEG unit to service the several work areas.

4. The improvement in the video telecommunication system as defined in claim 3, wherein the several work areas constitute separate areas of a unitary conference table.

5. The improvement in the video telecommunication system as defined in claim 4, wherein at least one work area has a panel section, with a video camera beneath it for viewing tables, graphs and other visual aids being used by the conferees.

6. The improvement in the video telecommunication system as defined in claim 1, wherein said means for illumination of the occupants of the work areas include a lower and upper light source means, wherein the light sources are colored red, orange, yellow, green, blue and violet and have one left-to-right orientation in the lower light source and the reverse orientation in the upper light source.

7. The improvement in the video telecommunication system as defined in claim 6, wherein the intensity of the white light, and of the colored lights collectively in the adjusted balance of relative intensities, being adjusted for optimum illumination for the television camera means.

8. The improvement in the video telecommunication system as defined in claim 1, wherein the synthetic sound generators include means for providing for continuous variation of the pitch and rhythm of the generated sound between finite limits.

9. The improvement in the video telecommunication system as defined in claim 1, wherein each said control panel includes a third button to be activated, when the respective conferee plans an extensive discourse, for switching the television camera means from panoramic viewing to enlarged viewing of the respective conferee and for activating a projection on a portion of the second television screen at both stations, of the alpha rhythm pattern of said conferee.

10. The improvement in the video telecommunication system as defined in claim 1, wherein a section of the second television screen is utilized to periodically project computer generated graphics said graphics generated by said versatile computer means based on the EEG readings of the participating conferees of each station so as to provide a real time portrayal of the progress of the conference with respects to an agreement of the conferees.

11. The improvement claimed in claim 10, wherein said graphics at a first stage comprises a square formed by first and second triangles joined at their bases and representing substantial synchronization of the left and right hemispheres of the brain the alpha level for the conferees, said substantial synchronization first occuring during the pre-conference mode after conditioning by said illumination means and said sound generation means, said graphics including first indicia indicating thought impulses originating in the left hemisphere, and reacted to by the right hemisphere, second indicia indicating thought impulses originating in the right hemisphere and reacted to by the left hemisphere, third indicia representing paths of inter-communication between the two hemispheres, said graphics further including a vertical line dividing the square into left and right triangles and producing in effect, third, fourth, fifth, and sixth smaller triangles, said third triangle representing conscious decompression, said fourth triangle representing conscious compression, said fifth triangle representing unconscious decompression, and said sixth triangle representing unconscious compression, said third and fifth triangles remaining unchanged in size throughout the conference while said fourth and sixth triangles vary in size in response to the varying EEG inputs to said computer means based on the reduction of alpha rhythm and increase in beta rhythm in the left brain hemispheres during the conference, after the pre-conference stage, said graphics including fourth and fifth indicia at opposite ends of the horizontal line formed at the bases of said first and second triangles, said fourth and fifth indicia comprising respective scale means which permit a visual indication of the extent of the change in size of said fourth and sixth triangles and thus the extent, or lack thereof, of progress towards a meeting of the minds of the conferees.

12. The improvement claimed in claim 1 wherein said camera means includes means for permanently recording the signals being generated.

* * * * *